United States Patent
Yuan et al.

(10) Patent No.: US 11,179,467 B2
(45) Date of Patent: Nov. 23, 2021

(54) EXENATIDE MODIFIER AND USE THEREOF

(71) Applicant: BRIGHTGENE BIO-MEDICAL TECHNOLOGY CO., LTD., Jiangsu (CN)

(72) Inventors: Jiandong Yuan, Suzhou (CN); Yangqing Huang, Suzhou (CN); Yunsong Song, Suzhou (CN); Fang Yuan, Suzhou (CN)

(73) Assignee: BRIGHTGENE BIO-MEDICAL TECHNOLOGY CO., LTD., Suzhou (CN)

( * ) Notice: Subject to any disclaimer, the term of this patent is extended or adjusted under 35 U.S.C. 154(b) by 192 days.

(21) Appl. No.: 15/752,838

(22) PCT Filed: Sep. 13, 2016

(86) PCT No.: PCT/CN2016/098844
§ 371 (c)(1),
(2) Date: Feb. 14, 2018

(87) PCT Pub. No.: WO2017/050157
PCT Pub. Date: Mar. 30, 2017

(65) Prior Publication Data
US 2020/0101162 A1 Apr. 2, 2020

(30) Foreign Application Priority Data
Sep. 25, 2015 (CN) .......................... 201510619012.7

(51) Int. Cl.
*A61K 47/14* (2017.01)
*A61P 3/10* (2006.01)
*A61K 38/26* (2006.01)

(52) U.S. Cl.
CPC .............. *A61K 47/14* (2013.01); *A61K 38/26* (2013.01); *A61P 3/10* (2018.01)

(58) Field of Classification Search
None
See application file for complete search history.

(56) References Cited

U.S. PATENT DOCUMENTS

| | | | |
|---|---|---|---|
| 2010/0184641 A1 | 7/2010 | Dorwald et al. | |
| 2011/0053848 A1 | 3/2011 | Cleemann et al. | |
| 2011/0171164 A1* | 7/2011 | Bossard ............... | C07K 14/605 424/78.17 |
| 2012/0196795 A1 | 8/2012 | Xu et al. | |
| 2013/0189328 A1 | 7/2013 | Cleemann et al. | |
| 2013/0310310 A1 | 11/2013 | Liu et al. | |

FOREIGN PATENT DOCUMENTS

| | | |
|---|---|---|
| CN | 1384755 A | 12/2002 |
| CN | 101125207 A | 2/2008 |
| CN | 101128214 A | 2/2008 |
| CN | 101215324 A | 7/2008 |
| CN | 101980725 A | 2/2011 |
| CN | 102397558 A | 4/2012 |
| CN | 102421796 A | 4/2012 |
| CN | 102532303 A | 7/2012 |
| CN | 102827270 A | 12/2012 |
| CN | 103237561 A | 8/2013 |
| WO | WO 99/43708 A1 | 9/1999 |
| WO | WO 00/41546 A2 | 7/2000 |
| WO | WO 2005/028516 A2 | 3/2005 |
| WO | WO 2006/097538 A1 | 9/2006 |
| WO | WO 2008/058461 A1 | 5/2008 |
| WO | WO 2009/095479 A2 | 8/2009 |
| WO | WO 2012/035139 A1 | 3/2012 |
| WO | WO 2013/059323 A1 | 4/2013 |

OTHER PUBLICATIONS

Lorenz et al. ('Recent progress and future options in the development of GLP-1 receptor agonists for the treatment of diabesity' Bioorganic and Medicinal Chemistry Letters v23 2013 pp. 4011-4018) (Year: 2013).*
Meloun et al. ('Complete amino acid sequence of human serum albumin' FEBS Letters v58(1) Oct. 1975 pp. 134-137) (Year: 1975).*
Schmitt et al. ('Intravitreal pharmacokinetics in mice: SPECT/CT imaging and scaling to rabbits and humans' Molecular Pharmaceutics v16 2019 pp. 4399-4404) (Year: 2019).*
Chae et al., "The fatty acid conjugated exendin-4 analogs for type 2 antidiabetic therapeutics," Journal of Controlled Release, vol. 144, No. 1, 2010, pp. 10-16.
Extended European Search Report for Application No. 16848039.0, dated Apr. 13, 2018.
Kong et al., "Long acting hyaluronate—exendin 4 conjugate for the treatment of type 2 diabetes," Biomaterials, vol. 31, No. 14, 2010, pp. 4121-4128.
Lee et al., "Preparation and evaluation of palmitic acid-conjugated exendin-4 with delayed absorption and prolonged circulation for longer hypoglycemia," International Journal of Pharmaceutics, vol. 424, Nos. 1-2, 2012, pp. 50-57.

(Continued)

*Primary Examiner* — Ronald T Niebauer
(74) *Attorney, Agent, or Firm* — Birch, Stewart, Kolasch & Birch, LLP

(57) ABSTRACT

Disclosed are an exenatide modifier for connecting the exenatide to a fatty chain with a carboxy in the terminus thereof by means of a hydrophilic connecting arm, and a use thereof in preparing drugs serving as a GLP-1 receptor agonist; a use in preparing drugs for preventing and/or treating diseases and/or symptoms associated with a low GLP-1 receptor activity; a use in preparing drugs for diseases and/or symptoms associated with glycometabolism; a use in preparing drugs for diabetes; a use in preparing drugs for fatty liver disease, and a use in preparing drugs for losing weight.

2 Claims, No Drawings
Specification includes a Sequence Listing.

(56) References Cited

OTHER PUBLICATIONS

Shechter et al., "Newly designed modifier prolongs the action of short-lived peptides and proteins by allowing their binding to serum albumin." Bioconjuaate Chemistry, vol. 23. No. 8, 2012. pp. 1577-1586.
Zhou et al., "Preparation and PEGylation of exendin-4 peptide secreted from yeast Pichia pastoris," European Journal of Pharmaceutics and Biopharmaceutics, vol. 72, No. 2, 2009, pp. 412-417.
International Search Report for PCT/CN2016/098844 (PCT/ISA/210) dated Nov. 8, 2016.
Canadian Office Action dated Jun. 3, 2020 for Application 2,995,613.
Chinese Office Action and Search Repot dated Mar. 4, 2020 for Application No. 201510619012.7 with an English translation of the Office Action.

\* cited by examiner

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (39)..(39)
<223> OTHER INFORMATION: AMIDATION

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

EXENATIDE MODIFIER AND USE THEREOF

REFERENCE TO SEQUENCE LISTING SUBMITTED VIA EFS-WEB

This application includes an electronically submitted sequence listing in .txt format. The .txt file contains a sequence listing entitled "5658-0131PUS1_ST25.txt" created on Dec. 4, 2019 and is 847 bytes in size. The sequence listing contained in this .txt file is part of the specification and is hereby incorporated by reference herein in its entirety.

FIELD

The present invention relates to the field of therapeutic peptides, particularly relates to exenatide modifiers, their preparation, a pharmaceutical composition containing the same, and the use of the modifiers and composition in the treatment of diseases associated with glycometabolism.

BACKGROUND

Exenatide (or Exendin-4, trade name by Byetta) is a polypeptide of 39 amino acids with a molecular weight of 4186.6, the molecular formula of which is $C_{184}H_{282}N_{50}O_{60}S$, and the amino acid sequence is: His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2 (SEQ ID NO: 1); which is produced and sold by Amylin Pharmaceuticals and Eli Lilly company (Eli Lillyand Company). Exenatide has been approved by FDA in April 2005, which belongs to subcutaneous injection preparation, with effects of promoting the glucose-dependent insulin secretion, recovering the insulin secretion of the first phase, inhibiting the glucagon secretion, slowing the emptying of gastric contents, improving the function of pancreatic β cells, and the like, being very useful in the treatment of type II diabetes, for example, to improve and control the blood glucose of patients with type II diabetes which are not ideal when treated by metformin and sulfonylurea drugs.

Exenatide is a synthetic form of the hormone, exendin-4, in the saliva of lizard, *Heloderma suspectum* (Gilamonster) grown in several states in the southwestern United States (J. Biol. Chem. 1990, 265, 20259-20262; J. Biol. Chem. 1992, 267, 7402-7405), which is an analogue of human glucagon-like peptide-1 (GLP-1), the amino acid sequence of which is partially overlapped with the amino acid sequence of GLP-1, being a potent GLP-1 receptor agonist, and also being known as an incretin agonist since that exenatide simulates the glucose regulation effect of GLP-1. Unlike sulfonylureas and meglitinides, exenatide increases the synthesis and secretion of insulin only in the presence of glucose, reducing the risk of hypoglycemia. Some physicians will also use Byetta in the treatment of insulin resistance.

Nevertheless, properties such as short half-life in vivo, poor physical and chemical stabilities, susceptible to degradation by various proteases in vivo are common in the protein/polypeptide drugs, such that these drugs often require multiple injections in a day, bring patients lots of pain and inconvenience. PEGylation emerged in 1970s has been proven to be a technology suitable for the field of the current administration of proteins/polypeptides. However, after being modified simply using PEG, the activities of drugs will generally decline.

A series of different methods have been used to modify the structures of GLP-1 analogues, so as to provide a longer duration of action in vivo. CN 1384755 discloses novel exendin agonist preparations and their dosing methods, which discloses the compound structure of exenatide and its preparation. CN 102532303 discloses the method of synthesizing exenatide conjugated with polyethylene glycol, by conjugating the methoxy polyethylene glycol residue with the amino of lysine residue in the molecule of exenatide or the amino of the histidine residue at the N terminal; CN101980725 discloses the structure of fatty acid-PEG-exenatide, with the modification site of PEG on the N terminal of His; WO2005028516 and WO2012035139 also disclose the structure of fatty acid-PEG-exenatide. Chinese patent CN 101215324 discloses a mimetic peptide of short exenatide peptide obtaining from the restructuring of exenatide. Chinese patent CN101125207 reports the PEG modification on Exendin-4. WO99/43708 discloses the GLP-1 (7-35) and GLP-1 (7-36) derivatives with lipophilic substitutes linked to the amino acid residues at the C terminal. WO2013059323A1 discloses a PEG-conjugated exenatide and its preparation.

CN 102397558 discloses the use of PEG or PEG modification with methyl substitution at the terminal, after substituting some amino acids in exendin-4 for cysteine. CN102421796 discloses that one or more polyethylene glycols polymerize to the cysteine of exendin variants, discloses an exenatide in which one amino acid is substituted with a cysteine, and then modified with polyethylene glycol on the cysteine. CN102827270 discloses an exendin-4-Cys-PEG derivative, specifically introducing one cysteine at the C-terminal of the inactive area of the exenatide molecule, and coupling with maleimido polyethylene glycol, wherein it is terminated with methyl at the polyethylene glycol terminal.

Notwithstanding these efforts in so many aspects have been made, the current existing exendin-4 or its variants and various modifications still possess some drawbacks, including the high dosing frequency when used in vivo, bring patients great burdens on their body, mentality and economy, restricting the compliance of patients, and being incapable of widely application. There remains a great requirement on the active long-acting GLP-1 analogues for diabetic populations, so it is a need to develop new exenatide derivatives, making them with long durations of action, good stabilities, good hypoglycemic effects, while maintaining low toxicities and good activities.

SUMMARY

The present invention is to overcome the drawbacks of the presently disclosed exenatide modifiers GLP-1 receptor, with low binding force and short hypoglycemia duration, thus causing poor effects or frequent injections in clinical use.

It is known to those skilled in the art that, in the bioactive molecule with a conjugated polymeric group, the biological activity of the conjugated biological molecule will gradually decrease exponentially as the molecular weight of the conjugated group increases. It is also known to those skilled in the art that as the molecular weight of the polymeric group increases, the biological half-life and/or plasma half-life and the systematic drug exposure of the conjugated biological molecule will gradually prolong or increase.

It is discovered unexpectedly by those skilled in the present invention that, through the modification of exenatide by those skilled in the present invention, the pharmacokinetical properties have been improved, thus increasing the hypoglycemia duration. And compared with exenatide, the molecules of the present invention still retain most of the activities of GLP-1 receptor agonists, which means that the molecules of the present invention are high in the activity of the GLP-1 receptor agonist, and have long hypoglycemia duration, with a possibility of being drugs with long durations of action, good stabilities, and good hypoglycemic effects in the future clinical applications.

On the one hand, the present invention provides such an exenatide modifier or pharmaceutically acceptable salts thereof, as shown in formula (I):

(Ex-4)-L-Y    (I)

wherein, Ex-4 is Exendin-4; L is a hydrophilic linking arm for connecting Ex-4 with Y; Y is an aliphatic chain with a terminal carboxyl group.

Further, the present invention provides such an exenatide modifier:

$$\text{Exendin}_4-\overset{H}{N}-L'-\overset{H}{N}-Y,$$

wherein L' is a hydrophilic linking arm, preferably a hydrophilic chain containing an ether group.

Furthermore, in the exenatide modifier (Ex-4)-L-Y of the present invention, the hydrophilic linking arm L is selected from:

(1), (2), (3), (4), (5), (6), (7), (8), (9), (10), (11), (12), (13), (14)

wherein m is any integer between 2-20; n is any integer between 2-20; r is any integer between 1-6.

Furthermore, the present invention provides such an exenatide modifier:

$$\text{Exendin}_4-\overset{H}{N}-L'-\overset{H}{N}-(\ )_k-COOH,$$

wherein L' is a hydrophilic chain containing an ether group, k is any integer between 6-20.

The specific structure (SEQ ID NO: 1) is as follows:
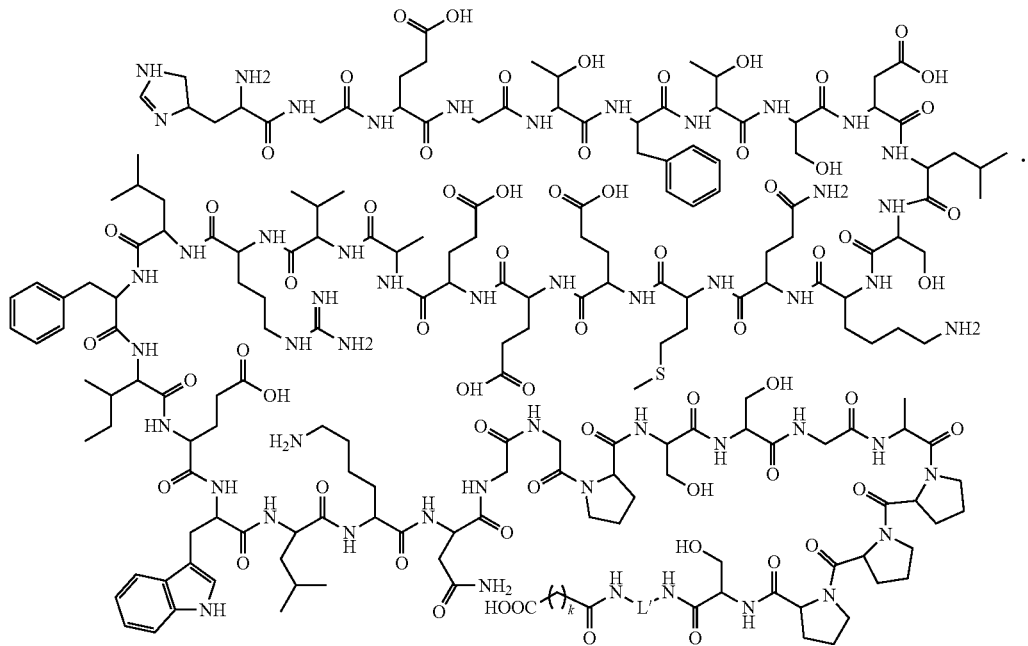
The present invention preferably provides such exenatide modifiers:
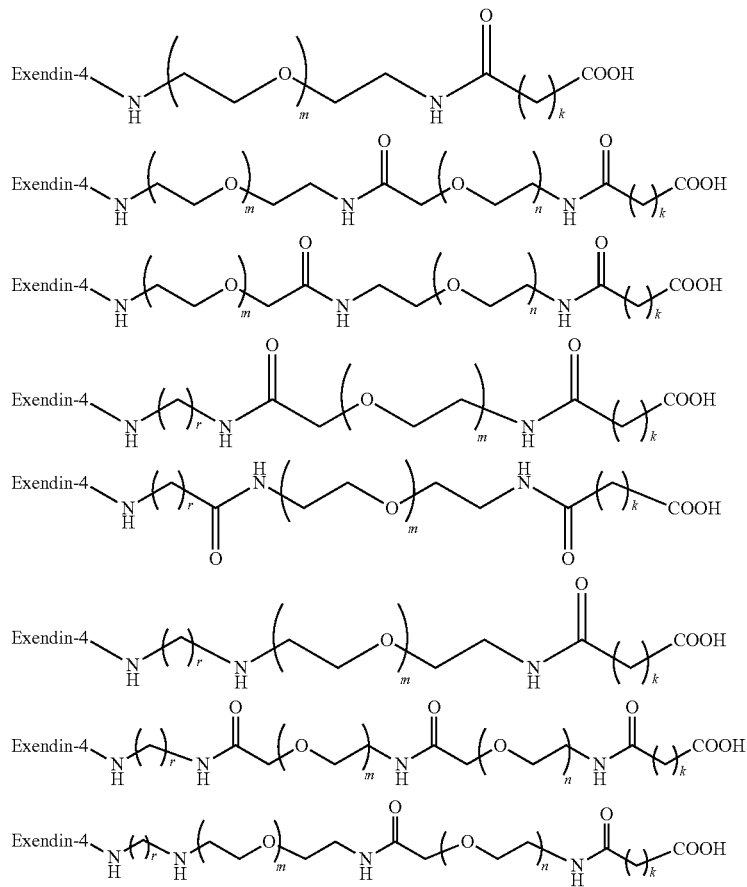

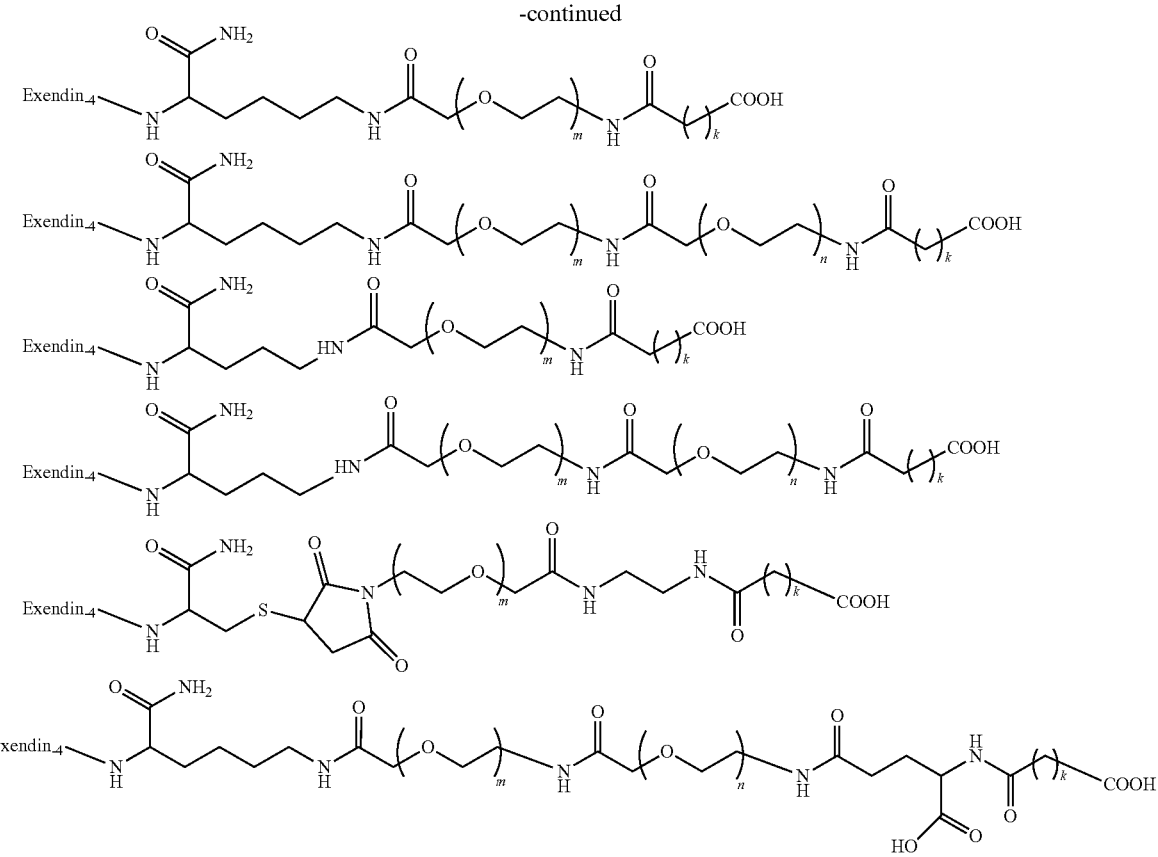

wherein m is any integer between 2-20; n is any integer between 2-20; r is any integer between 1-6; k is any integer between 6-20.

More specifically, the present invention provides the following exenatide modifiers:

Series 1: See Examples 1-5

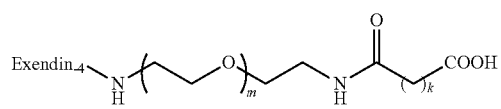

| Com-<br>pound | Com-<br>pound 1 | Com-<br>pound 2 | Com-<br>pound 3 | Com-<br>pound 4 | Com-<br>pound 5 |
|---|---|---|---|---|---|
| m | 5 | 2 | 20 | 14 | 10 |
| k | 16 | 20 | 6 | 10 | 14 |

Series 2: See Examples 6-10

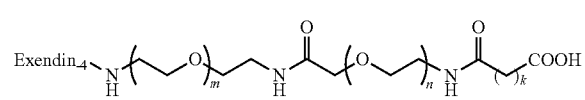

| Com-<br>pound | Com-<br>pound 6 | Com-<br>pound 7 | Com-<br>pound 8 | Com-<br>pound 9 | Com-<br>pound 10 |
|---|---|---|---|---|---|
| m | 5 | 2 | 20 | 10 | 11 |
| n | 3 | 7 | 2 | 20 | 15 |
| k | 16 | 20 | 12 | 6 | 10 |

Series 3: See Examples 11-15

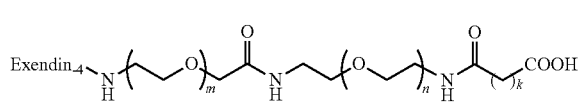

| Com-<br>pound | Com-<br>pound 11 | Com-<br>pound 12 | Com-<br>pound 13 | Com-<br>pound 14 | Com-<br>pound 15 |
|---|---|---|---|---|---|
| m | 3 | 2 | 20 | 10 | 11 |
| n | 5 | 9 | 2 | 20 | 15 |
| k | 16 | 20 | 12 | 6 | 10 |

Series 4: See Examples 16-20

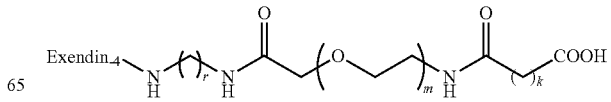

| Compound | Compound 16 | Compound 17 | Compound 18 | Compound 19 | Compound 20 |
|---|---|---|---|---|---|
| r | 2 | 3 | 3 | 3 | 6 |
| m | 6 | 2 | 15 | 10 | 20 |
| k | 16 | 18 | 10 | 20 | 6 |

Series 5: See Examples 21-25

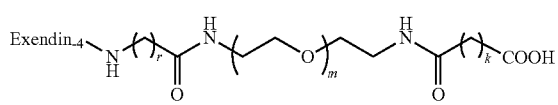

| Compound | Compound 21 | Compound 22 | Compound 23 | Compound 24 | Compound 25 |
|---|---|---|---|---|---|
| r | 1 | 2 | 3 | 3 | 6 |
| m | 5 | 2 | 15 | 10 | 20 |
| k | 16 | 18 | 10 | 20 | 6 |

Series 6: See Examples 26-30

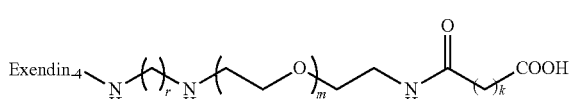

| Compound | Compound 26 | Compound 27 | Compound 28 | Compound 29 | Compound 30 |
|---|---|---|---|---|---|
| r | 2 | 2 | 3 | 3 | 6 |
| m | 5 | 2 | 15 | 10 | 20 |
| k | 16 | 14 | 10 | 20 | 6 |

Series 7: See Examples 31-35

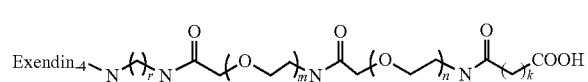

| Compound | Compound 31 | Compound 32 | Compound 33 | Compound 34 | Compound 35 |
|---|---|---|---|---|---|
| r | 2 | 2 | 3 | 3 | 6 |
| m | 6 | 2 | 15 | 10 | 20 |

| Compound | Compound 31 | Compound 32 | Compound 33 | Compound 34 | Compound 35 |
|---|---|---|---|---|---|
| n | 3 | 20 | 5 | 10 | 2 |
| k | 16 | 14 | 10 | 20 | 6 |

Series 8: See Examples 36-40

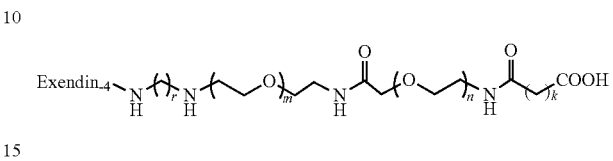

| Compound | Compound 36 | Compound 37 | Compound 38 | Compound 39 | Compound 40 |
|---|---|---|---|---|---|
| r | 2 | 2 | 3 | 3 | 6 |
| m | 5 | 2 | 15 | 10 | 20 |
| n | 6 | 20 | 5 | 10 | 2 |
| k | 16 | 14 | 10 | 20 | 6 |

Series 9: See Examples 41-45

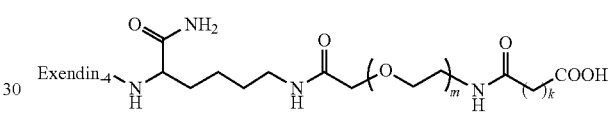

| Compound | Compound 41 | Compound 42 | Compound 43 | Compound 44 | Compound 45 |
|---|---|---|---|---|---|
| m | 6 | 2 | 20 | 10 | 15 |
| k | 16 | 14 | 10 | 20 | 6 |

Series 10: See Examples 46-50

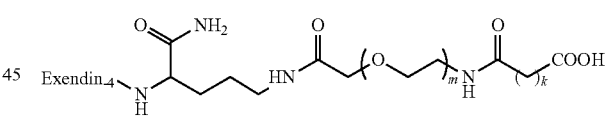

| Compound | Compound 46 | Compound 47 | Compound 48 | Compound 49 | Compound 50 |
|---|---|---|---|---|---|
| m | 6 | 2 | 20 | 10 | 15 |
| k | 16 | 14 | 10 | 20 | 6 |

Series 11: See Examples 51-55

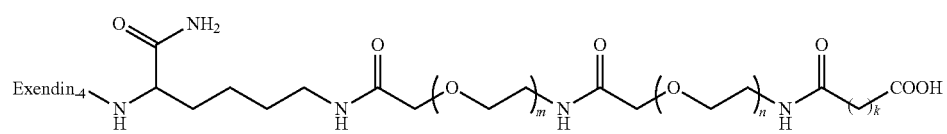

| Compound | Compound 51 | Compound 52 | Compound 53 | Compound 54 | Compound 55 |
|---|---|---|---|---|---|
| m | 6 | 2 | 20 | 10 | 15 |
| n | 3 | 9 | 16 | 2 | 20 |
| k | 16 | 14 | 10 | 20 | 6 |

Series 12: See Examples 56-60

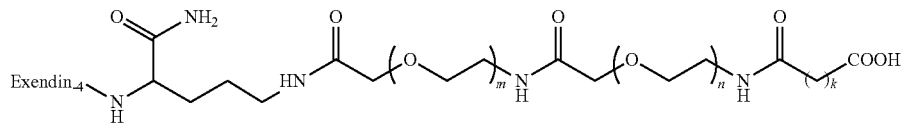

| Compound | Compound 56 | Compound 57 | Compound 58 | Compound 59 | Compound 60 |
|---|---|---|---|---|---|
| m | 6 | 2 | 20 | 10 | 15 |
| n | 3 | 9 | 16 | 2 | 20 |
| k | 16 | 14 | 10 | 20 | 6 |

Series 13: See Examples 61-66

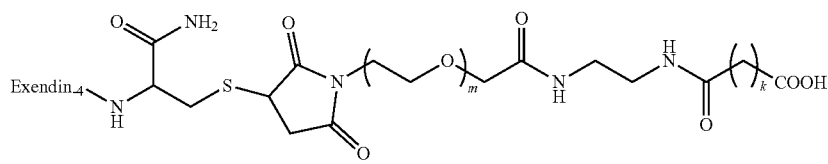

| Compound | Compound 61 | Compound 62 | Compound 63 | Compound 64 | Compound 65 | Compound 66 |
|---|---|---|---|---|---|---|
| m | 2 | 4 | 5 | 7 | 9 | 10 |
| k | 20 | 10 | 16 | 8 | 16 | 6 |

Series 14: See Example 67

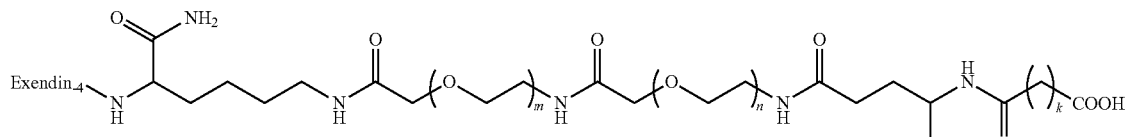

$m = 6; n = 3; k = 16$

On the other hand, the present invention provides a use of the exenatide modifier or pharmaceutically acceptable salts thereof in preparing drugs serving as a GLP-1 receptor agonist, a use in preparing drugs for preventing and/or treating diseases and/or symptoms associated with a low GLP-1 receptor activity, a use in preparing drugs for diseases and/or symptoms associated with glycometabolism, a use in preparing drugs for diabetes, a use in preparing drugs for fatty liver, and a use in preparing drugs for losing weight.

In the third aspect, the present invention provides a composition comprising an exenatide modifier or pharmaceutically acceptable salts thereof and optionally pharmaceutically acceptable carriers.

In the fourth aspect, the present invention provides a use of the above described composition in preparing drugs serving as a GLP-1 receptor agonist, a use in preparing drugs for preventing and/or treating diseases and/or symptoms associated with a low GLP-1 receptor activity, a use in preparing drugs for diseases and/or symptoms associated with glycometabolism, a use in preparing drugs for diabetes, a use in preparing drugs for fatty liver, and a use in preparing drugs for losing weight.

The exenatide modifiers provided in the present invention not only possess higher GLP-1 receptor agonistic activities, but also long durations of hypoglycemia. It is illustrated through the following pharmacological tests.

Each test sample was respectively dissolved in double distilled water to a final concentration of $1.0 \times 10^{-2}$ mol/L, and stored at 4° C. PC 12 cells were cultured in a 25 cm² culture flask placed in the $CO_2$ incubator (37° C., 95% air, 5% $CO_2$), with the culture medium of DMEM (Dulbecco's Modified Eagle's Medium, pH=7.4, high glucose), in which there were added 5% fetal bovine serum and 10% horse serum. The well-grown PC 12 cells were digested with 0.25% pancreatin, the cell concentration being adjusted to $1.0 \times 10^5$ cells/ml, seeded in a 24-well plate. When cells grew to the density of 60-70%, they were washed twice with PBS (Phosphate Buffer Saline) with the addition of PBS containing 1% BSA (Bovine Serum Albumin) for 1 ml each, and the test drugs were respectively divided into 5 gradients of concentration ($10^{-10}$, $10^{-9}$, $10^{-8}$, $10^{-7}$, $10^{-6}$ mol/L) and co-incubated with IBMX (3-isobutyl-1-methylxanthine, 100 µmol/L) for 30 min, 3 operations of multiple holes being done for each concentration of the samples. Once the intervention time of drugs end, the cells were collected immediately, suspended with cold PBS, and the cell concentration was adjusted to 1.0×10⁷/ml. One volume of 1N HCl was immediately added into 9 volumes of cell suspension, incubated for 10 min at room temperature, ultrasonicated with an ultrasonic apparatus for 15 s. At 4° C., they were centrifuged for 10 min at 1000 rpm to remove cell debris. The supernatant was added into 1N NaOH of equal volume with 1N HCl to neutralization (wherein 1N represents one equivalent), the resulting solution being the sample solution containing cAMP, stored at −20° C. ready for detection. Non-Interference Protein Assay Kit was employed to detect the total protein concentration in the sample. The content of cAMP in the cell lysate was detected using ELISA kit following the instruction of the kit, and the OD (Optical Density) value was determined at 450 nm by the BIO-RAD 680 Microplate Reader. Based on the OD value of the standard, CurveExpert 1.3 software was employed to fit curves and compute the standard curve formula, and calculate the concentration of each sample. Computer programs Microsoft Excel and GraphPad Prism 5 software were used for data processing and charting to calculate $EC_{50}$ (half effective concentration, Concentration for 50% of Maximal Effect) of each test drug.

TABLE

Effects of the compounds on the cAMP activities in cells

| Compound | $EC_{50}$ |
|---|---|
| 1 | 5.879 |
| 2 | 6.423 |
| 3 | 6.174 |
| 4 | 6.075 |
| 5 | 6.278 |
| 6 | 6.346 |
| 7 | 7.217 |
| 8 | 7.064 |
| 9 | 5.974 |
| 10 | 6.127 |
| 11 | 7.236 |
| 12 | 8.042 |
| 13 | 7.578 |
| 14 | 7.642 |
| 15 | 7.539 |
| 16 | 8.742 |
| 17 | 9.416 |
| 18 | 7.753 |
| 19 | 7.942 |
| 20 | 8.363 |
| 21 | 8.567 |
| 22 | 9.642 |
| 23 | 8.014 |
| 24 | 7.963 |
| 25 | 8.257 |
| 26 | 8.019 |
| 27 | 8.742 |
| 28 | 7.878 |
| 29 | 8.042 |
| 30 | 8.173 |
| 31 | 8.425 |
| 32 | 8.053 |
| 33 | 8.172 |
| 34 | 8.345 |
| 35 | 8.296 |
| 36 | 8.247 |
| 37 | 7.942 |
| 38 | 8.296 |
| 39 | 8.472 |
| 40 | 8.257 |
| 41 | 5.554 |
| 42 | 5.872 |
| 43 | 5.742 |
| 44 | 6.117 |
| 45 | 6.204 |
| 46 | 5.674 |
| 47 | 5.916 |

TABLE-continued

Effects of the compounds on the cAMP activities in cells

| Compound | $EC_{50}$ |
|---|---|
| 48 | 5.705 |
| 49 | 6.342 |
| 50 | 6.154 |
| 51 | 5.341 |
| 52 | 5.462 |
| 53 | 5.674 |
| 54 | 5.553 |
| 55 | 5.697 |
| 56 | 6.247 |
| 57 | 5.969 |
| 58 | 6.374 |
| 59 | 6.545 |
| 60 | 6.278 |
| 61 | 6.212 |
| 62 | 5.774 |
| 63 | 5.692 |
| 64 | 5.726 |
| 65 | 5.948 |
| 66 | 5.970 |
| 67 | 5.742 |
| Exendin-4 | 5.096 nmol/L |

After binding, GLP-1 and GLP-1 receptors (G coupling proteins of β receptor family) activate cyclic adenosine monophosphate (cAMP) and mitogen-activated protein kinase (MAPK) pathway. GLP-1 receptors of mature pancreatic β cells coupled with Gs, activating the adenylate cyclase and producing cAMP, the latter, coordinated with glucose, stimulating the synthesis and secretion of insulin, stimulating the gene transcription of insulin and the biosynthesis of proinsulin, reducing the glucagon concentration and inhibiting the secretion of glucagon, enhancing the sensitivity of cells on insulin, stimulating the insulin-dependent glycogen synthesis, reducing the postprandial blood sugar concentration. The smaller the $EC_{50}$ was, indicating the higher drug GLP-1 receptor agonistic activities.

It was shown from the results in Table 1 that, the compounds of the present invention were comparable to exenatide in activity or only slightly decreased, indicating that the modifications on exenatide in the present invention have no influences on the GLP-1 receptor agonistic activities.

Hypoglycemic Effects on Spontaneous Type 2 Diabetes Db/Db Mice

C57BL/6db/db9 mice (male) at the age of 5-6 weeks were purchased from Model Animal Research Center of Nanjing University, the experimental animals being feed in the SPF animal houses. The animal houses were well-ventilated, equipped with air conditioners, keeping the temperature at 20~25° C. and the humidity at 40%~70%, with the ventilation rate of 10~15 times/h, light and dark each for 12 hours. Experimental animals had free access to food and water, and each mouse was marked with an ear tag. Mice were used in the experiment once a week, with the period of no more than three weeks. After one week acclimation, the capillary blood glucoses at the tail tip of mice were determined by MAJOR glucose meter. 340 mice with blood glucose level greater than 16.7 mmol/L were chosen and randomly grouped into 68 groups according to the blood glucose level. The model control group was given 5 mL/kg PBS (pH=7.4) by subcutaneous injection, the positive control group 1 was given Exenatide (10 µg/kg, 5 mL/kg) by subcutaneous injection, the dosing groups were respectively injected compounds 1-15 (10 µg/kg, 5 mL/kg) subcutaneously. After administration, the blood glucoses at 0, 1, 2, 4, 8, 12, 18, 24, 30, 36, 42, 48, 72 h were determined by a glucose meter, and all data was input into Graphpad Prism to calculate the mean blood glucose. The maximum hypoglycemic effect (the maximum reduction rate compared with the model group), the maximum hypoglycemic time (the last time point at which the blood glucose decreased significantly compared with the model group), and the area under the curve were calculated.

TABLE 2

Hypoglycemic effects on spontaneous type 2 diabetes db/db mice (h)

| Compound | Maximum hypoglycemic time |
| --- | --- |
| 1 | 36 |
| 2 | 36 |
| 3 | 30 |
| 4 | 36 |
| 5 | 42 |
| 6 | 36 |
| 7 | 42 |
| 8 | 42 |
| 9 | 36 |
| 10 | 36 |
| 11 | 30 |
| 12 | 42 |
| 13 | 36 |
| 14 | 30 |
| 15 | 36 |
| 16 | 36 |
| 17 | 42 |
| 18 | 42 |
| 19 | 48 |
| 20 | 30 |
| 21 | 48 |
| 22 | 48 |
| 23 | 42 |
| 24 | 42 |
| 25 | 36 |
| 26 | 36 |
| 27 | 30 |
| 28 | 36 |
| 29 | 42 |
| 30 | 30 |
| 31 | 36 |
| 32 | 36 |
| 33 | 30 |
| 34 | 48 |
| 35 | 30 |
| 36 | 42 |
| 37 | 42 |
| 38 | 36 |
| 39 | 48 |
| 40 | 36 |
| 41 | 42 |
| 42 | 42 |
| 43 | 42 |
| 44 | 48 |
| 45 | 30 |
| 46 | 42 |
| 47 | 42 |
| 48 | 48 |
| 49 | 48 |
| 50 | 36 |
| 51 | 48 |
| 52 | 48 |
| 53 | 42 |
| 54 | 48 |
| 55 | 42 |
| 56 | 48 |
| 57 | 48 |
| 58 | 42 |
| 59 | 48 |
| 60 | 42 |
| 61 | 48 |
| 62 | 42 |
| 63 | 48 |
| 64 | 36 |
| 65 | 40 |
| 66 | 36 |
| 67 | 42 |
| Exendin-4 | 4 |

It was shown from the results in Table 2 that compared with Exenatide, the compounds of the present invention have a great advantage in terms of maintaining the hypoglycemia time, prolonging the maximum hypoglycemic time from 4 h to 30 h-48 h.

Based on the results of the above two tests, the preferred compounds of the present invention are compounds 41, 42, 43, 46, 47, 48, 51-63, 65, 67.

In summary, the exenatide modifiers of the present invention were comparable to exenatide in activity or only slightly decreased, retained most of the GLP-1 receptor agonistic activities, and the modifications on exenatide had no influences on the GLP-1 receptor agonistic activities. Meanwhile, the exenatide modifiers of the present invention have a great advantage in terms of maintaining the hypoglycemia time, prolonging the maximum hypoglycemic time from 4 h to 30 h-48 h. The molecules of the present invention not only have high GLP-1 receptor agonistic activities, but also long hypoglycemia durations, with the possibility of becoming drugs with long action in vivo, good stabilities and good hypoglycemic effects in the future clinical applications.

SPECIFIC EXAMPLES

Amino acids and their abbreviations and short names in English are shown in the following table:

| Name | Protected Amino Acids | Abbreviation of three letters | Abbreviation of single letter |
| --- | --- | --- | --- |
| Alanine | Fmoc-Ala-OH | Ala | A |
| Aspartic acid | Fmoc-Asp(OtBu)-OH | Asp | D |
| Glutamic acid | Fmoc-Glu(OtBu)-OH | Glu | G |
| Phenylalanine | Fmoc-Phe-OH | Phe | F |
| Glycine | Fmoc-Gly-OH | Gly | G |
| Histidine | Fmoc-His(Trt)-OH | His | H |
| Isoleucine | Fmoc-Ile-OH | Ile | I |
| Lysine | Fmoc-Lys(Boc)-OH | Lys | K |
| Leucine | Fmoc-Leu-OH | Leu | L |
| Methionine | Fmoc-Met-OH | Met | M |
| Asparagine | Fmoc-Asn(Trt)-OH | Asn | N |
| Proline | Fmoc-Pro-OH | Pro | P |
| Glutamine | Fmoc-Gln(Trt)-OH | Gln | Q |
| Arginine | Fmoc-Arg (Pbf)-OH | Arg | R |
| Serine | Fmoc-Ser(tBu)-OH | Ser | S |
| Threonine | Fmoc-Thr(tBu)-OH | Thr | T |
| Valine | Fmoc-Val-OH | Val | V |
| Tryptophan | Fmoc-Trp(Boc)-OH | Trp | W |
| Tyrosine | Fmoc-Tyr(tBu)-OH | Tyr | Y |
| Lysine | Fmoc-Lys(Alloc)-OH | Lys | K |
| Ornithine | Fmoc-Orn(Alloc)-OH | Orn | |

Protected amino acids required in the Fmoc process solid-phase synthesis and their abbreviations

Example 1 Preparation of Compound 1

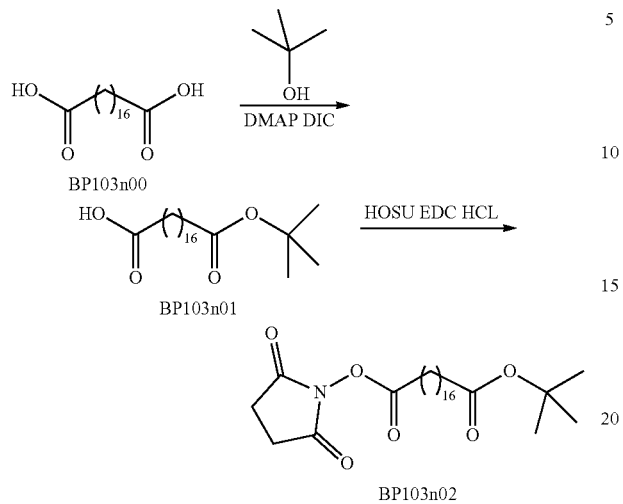

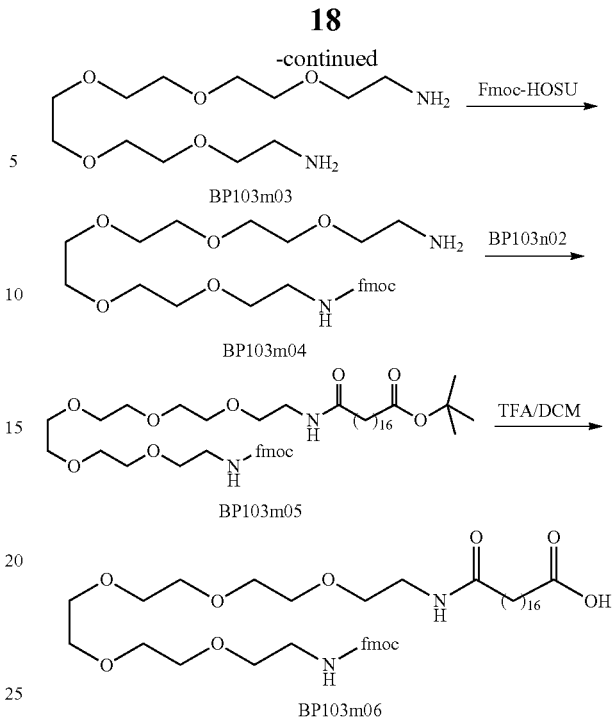

Preparation of BP103n01

To a 50 mL three-necked flask were added 1.0 g compound BP103n00 (1.0 eq, wherein eq represents the equivalent, the same below), 10 ml dichloromethane, 10 ml tert-butanol, 0.40 g DIC (1.0 eq), and 0.39 g DMAP (1.0 eq, 4-dimethylaminopyridine). They were stirred overnight at room temperature, monitored by TLC (thin-layer chromatography) until the completion of the reaction, diluted with ether, and then washed with water for 3 times, washed with saturated brine, dried over anhydrous sodium sulfate, and chromatographed in a column to give 10.4 g BP103n0 as a foamy powder.

Preparation of BP103n02

To a 100 mL three-necked flask were added 0.95 g N-hydroxy succinimide (HOSU), 2.0 g compound 19 and 15 ml dichloromethane, into which 1.58 g EDC.HCl was added and reacted for 2 h at room temperature. After the completion of the reaction under the monitor of TLC, they were diluted with dichloromethane, and then washed with 50 mmol/L aqueous solution of potassium dihydrogen phosphate at pH=6.0 for 2 times, washed with saturated brine, dried over anhydrous sodium sulfate, and concentrated to give 2.6 g compound BP103n02 as a white solid.

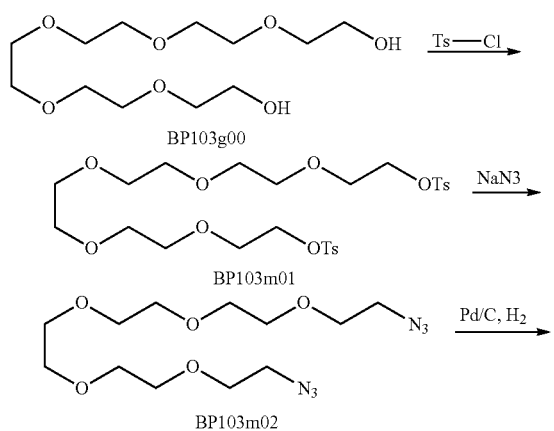

Preparation of BP103m01

Under the protection of nitrogen, to a 500 ml three-necked flask were added 200 mL pyridine, 50 g BP103g00 (1.0 eq), stirred and cooled down to 0° C. 70.7 g TsCl (2.1 eq) was added in batches, stirred for 1 h, and then slowly warmed up to room temperature, continuing to stir for 3-4 h. After the completion of the reaction, the reaction liquid was poured into the ice-cold solution of diluted hydrochloric acid, extracted with ethyl acetate. The ethyl acetate layer was washed once with diluted hydrochloric acid, washed with saturated sodium bicarbonate and saturated brine, and dried over anhydrous $Na_2SO_4$. The solvents were evaporated off at reduced pressure, and chromatographed in a silica gel column to give 52 g pure BP103m01.

Preparation of BP103m02

To a 500 mL three-necked flask were added 50 g BP103m01 (1.0 eq) and 150 mL DMSO (dimethyl sulfoxide), and stirred evenly, into which was then added $NaN_3$ 22.0 g (4.0 eq), heated to 50° C. and reacted for 3 hours, cooled down to room temperature. The reaction liquid was poured into water, extracted with ethyl acetate for many times. The organic phases were combined, dried over anhydrous sodium sulfate, and concentrated to give 25.3 g BP103m02 as a colourless liquid.

Preparation of BP103m03

To a 1 L hydrogenation reactor were added BP103m03 25 g, methanol 200 mL, palladium on carbon 6.0 g, stirred, with nitrogen replaced by introducing hydrogen to react for 3-4 h. After the completion of the reaction under the monitor of TLC, the reaction liquid was filtered, and the filtrate was concentrated to give 20.4 g BP103m03 as an oil.

Preparation of BP103m04

To a 500 mL three-necked flask were added compound BP103m03 20.0 g (1.0 eq), dichloromethane 200 ml, and Fmoc-HOSU 24.0 g (1.0 eq), stirred and cooled down to 0° C. 9.2 g DIEA (1.0 eq, N,N-diisopropyl ethylamine) was added dropwise, and stirred overnight. After the completion of the reaction under the monitor of TLC, it was washed with water and saturated brine, dried over anhydrous sodium sulfate, and then chromatographed in a column to give 27.3 g BP103m04 as an oil.

Preparation of BP103m05

To a 200 mL flask were added 5.0 g BP103m04 (1.0 eq), 50 ml water, 1.7 g NaHCO$_3$ (2.0 eq), and stirred. A solution of 4.7 g compound BP103n02 (1.0 eq) in 50 ml DME (ethylene glycol dimethyl ether) was added dropwise, replenished with 50 ml THF (tetrahydrofuran), and stirred overnight. After the completion of the reaction under the monitor of TLC, the organic solvents were evaporated off, adjusted to pH=4 with acetic acid, extracted with ethyl acetate, dried over anhydrous sodium sulfate, and concentrated to give 6.4 g compound BP103m05 as an off-white solid.

Preparation of BP103m06

To a 100 mL flask were added 6.0 g compound BP103m05, 30 ml dichloromethane, 30 ml TFA (trifluoroacetic acid), and stirred at 20° C. After the completion of the reaction under the monitor of TLC, the organic solvents were evaporated off, slurried in petroleum ether, suction filtrated, and dried to give 5.1 g BP103m06 as an off-white solid.

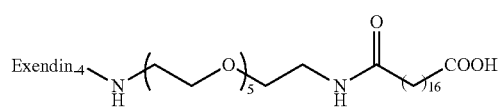

Synthesis of Target Compound

To a 20 ml reaction column were added 1.0 g 2Cl-Trt resin, 240 mg BP103m06, 5 ml dichloromethane, and 300 ul DIEA, into which nitrogen was bubbled for 40 min. 5 ml dichloromethane, 1 ml methanol, and 1 ml DIEA were added and reacted for 20 min, after which they were washed with DMF (N,N-dimethylformamide), producing BP103m06 resin. HOBT/DIC (i.e, 1-hydroxy benzotriazole/N,N-diisopropylcarbodiimide) was used as the coupling reagent, with DMF as the reactive solvent. The reaction was monitored by employing the ninhydrin detection method, successively connecting the following protected amino acids onto the resin: Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg (Pbf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Fmoc-His(Trt)-OH, with Fmoc protection finally removed. The pyrolysis of the resin was achieved by employing 82.5% TFA/5% phenol/5% water/ 2.5% EDT/5% thioanisole, and then they were precipitated with ice-cold methyl tert-butyl ether (MTBE), and washed, and crude products were purified by reverse HPLC to give 32 mg pure target peptide.

MS (ESI$^+$, m/e): 4743.53[M+H]$^+$

Example 2 Preparation of Compound 2

Compound 2 was prepared with reference to the method of Example 1:

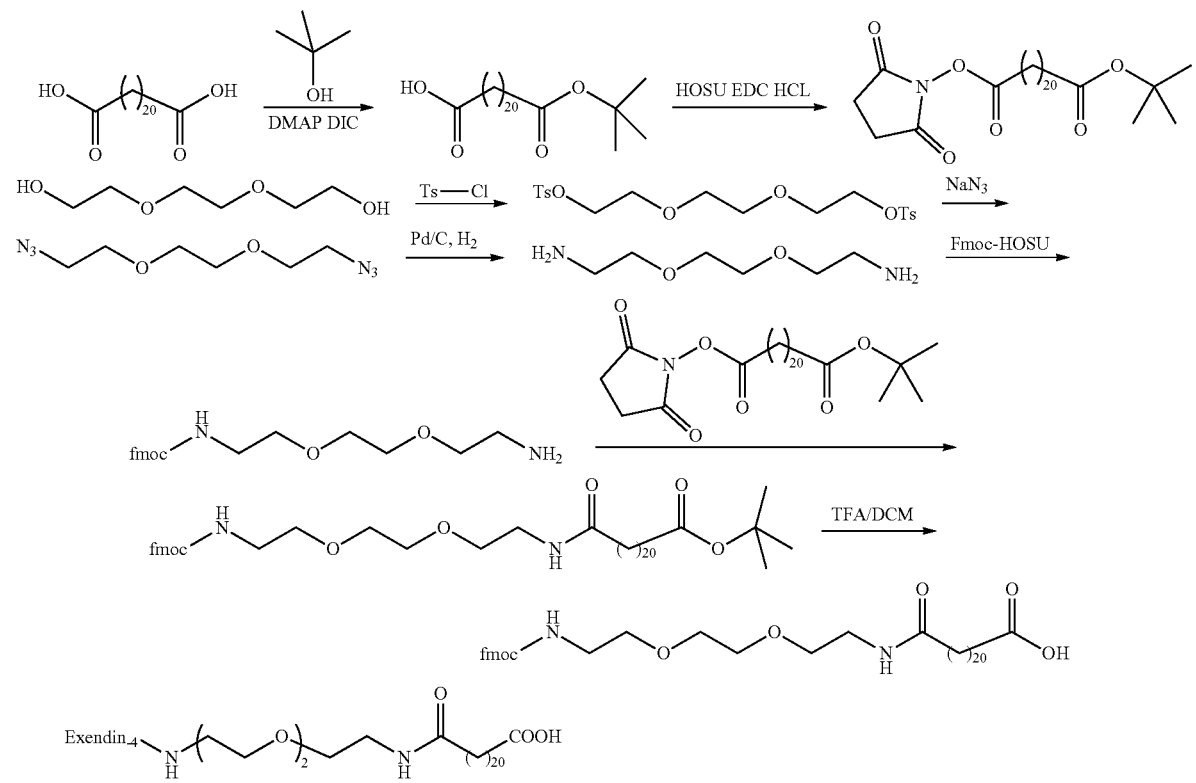

31.2 mg pure target peptide was finally obtained.
MS (ESI+, m/e): 4667.52[M+H]+

Example 3 Preparation of Compound 3

Compound 3 was prepared with reference to the method of Example 1:

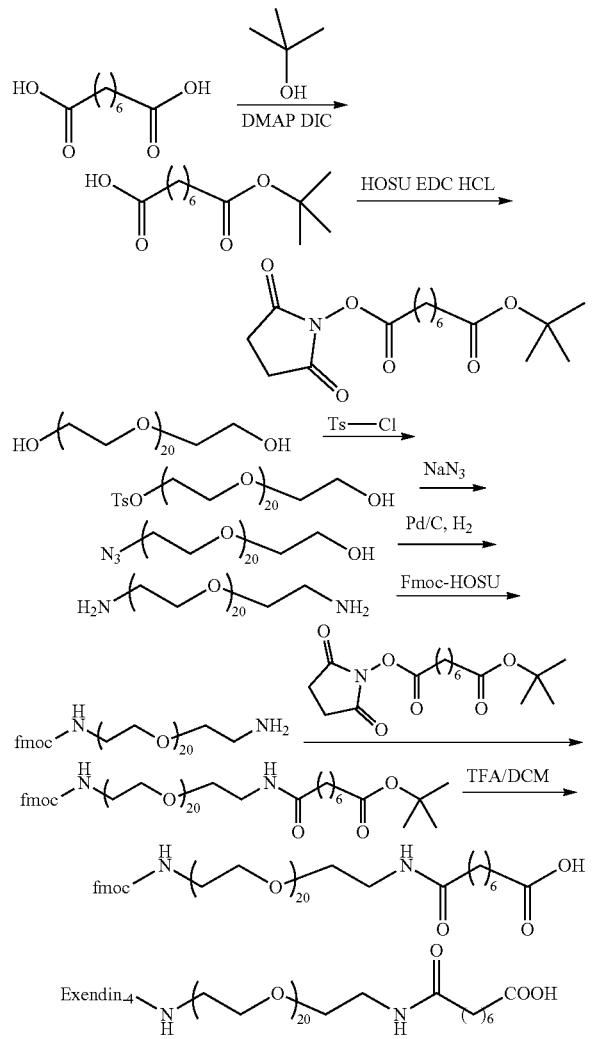

32.3 mg pure target peptide was finally obtained.
MS (ESI+, m/e): 5263.78[M+H]+

Example 4 Preparation of Compound 4

Compound 4 was prepared with reference to the method of Example 1:

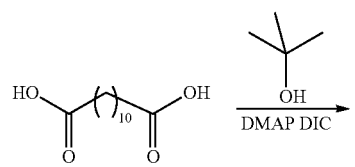

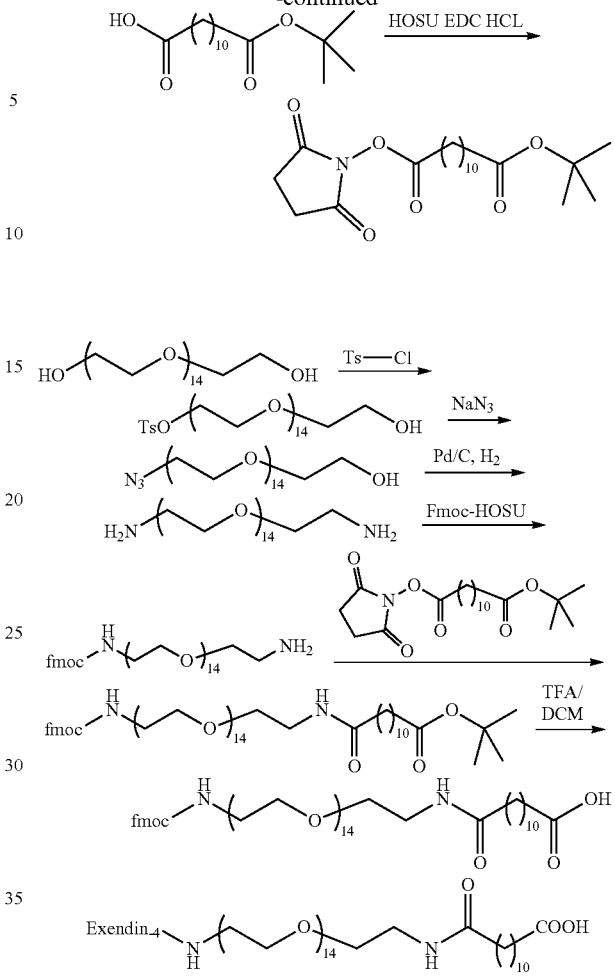

31.8 mg pure target peptide was finally obtained.
MS (ESI+, m/e): 5055.68[M+H]+

Example 5 Preparation of Compound 5

Compound 5 was prepared with reference to the method of Example 1:

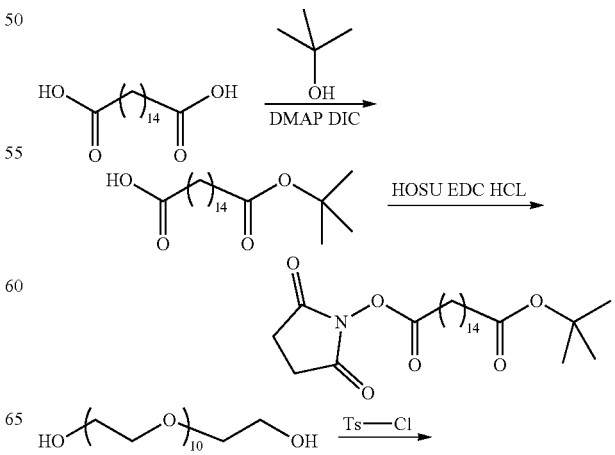

-continued

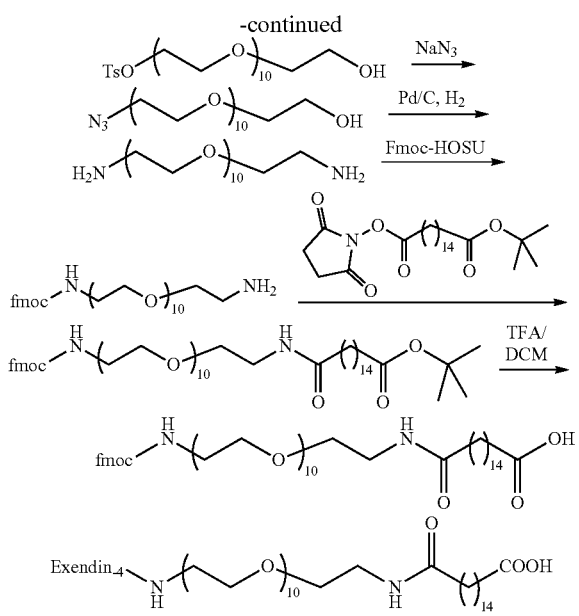

31.0 mg pure target peptide was finally obtained. MS (ESI⁺, m/e): 4935.64[M+H]⁺

Example 6 Preparation of Compound 6

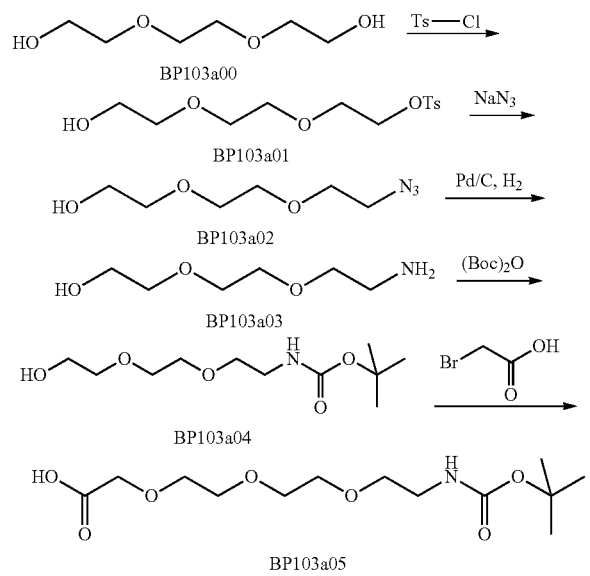

Preparation of BP103a01

Under the protection of nitrogen, to a 1000 ml three-necked flask were added 200 mL pyridine, 120 g BP103a00 (1.0 eq), stirred and cooled down to 0° C. 151.8 g TsCl (1.0 eq) was added in batches, stirred for 1 h, then slowly warmed up to room temperature, and kept stirring for 3-4 h. After the completion of the reaction, the reaction liquid was poured into ice-cold dilute hydrochloric acid solution, extracted with ethyl acetate. The ethyl acetate layer was washed once with dilute hydrochloric acid, washed with saturated sodium bicarbonate, washed with saturated brine, and dried over anhydrous $Na_2SO_4$. The solvents were evaporated off at reduced pressure, and chromatographed in a silica gel column to give 55 g pure BP103a01.

Preparation of BP103a02

To a 1000 mL three-necked flask were added 55 g BP103a01 (1.0 eq) and 160 mL DMSO, stirred evenly, in which was then added $NaN_3$ 23.52 g (2.0 eq), heated to 50° C. and reacted for 3 hours, and cooled down to room temperature. The reaction liquid was poured into water, extracted with ethyl acetate. The organic phases were combined, dried over anhydrous sodium sulfate, and concentrated to give 29.2 g BP103a02 as a colourless liquid.

Preparation of BP103a03

To a 1 L hydrogenation reactor were added 29 g BP103a02, methanol 360 mL, palladium on carbon 5.0 g, and stirred. Nitrogen was replaced, and hydrogen was introduced to react for 3-4 h. After the completion of the reaction under the monitor of TLC, the reaction liquid was filtered, and the filtrate was concentrated to give 23.5 g BP103a03 as an oil.

Preparation of BP103a04

To a 1 L three-necked flask were added 23.5 g compound BP103a03 (1.0 eq), 68.6 g $(Boc)_2O$ (2.0 eq), a mixed solution of methanol:triethylamine (9:1) 500 ml, stirred and warmed to reflux, and reacted for 1 h. After the completion of the reaction under the monitor of TLC, methanol triethylamine was evaporated off, and dissolved with water. Dichloromethane was extracted for 3 times. The organic layers were combined and washed once with water, dried over anhydrous sodium sulfate. The solvents were evaporated off, and dried to give 34.8 g BP103a04 as a solid.

Preparation of BP103a05

To a 1000 mL three-necked flask were added 34.8 g compound BP103a04 (1.0 eq), toluene and THF 150 ml for each, bromoacetic acid 58.2 g (3 eq), stirred, heated to 45-50° C., then added sodium hydroxide 33.5 g (6 eq), and reacted overnight. After the completion of the reaction under the monitor of TLC, the reaction liquid was evaporated off, extracted with water and ethyl acetate, and the aqueous phase was adjusted to pH 3. The aqueous phase was extracted with dichloromethane, and the dichloromethane layers were combined, dried over anhydrous sodium sulfate, and then concentrated to give 18 g BP103a05 compound as an oil.

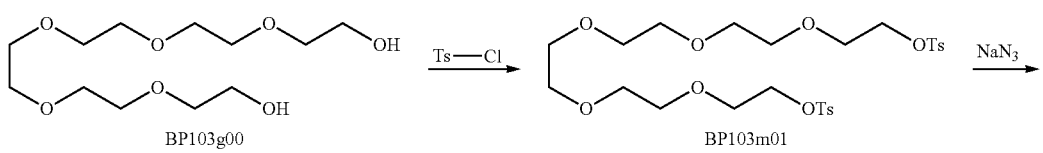

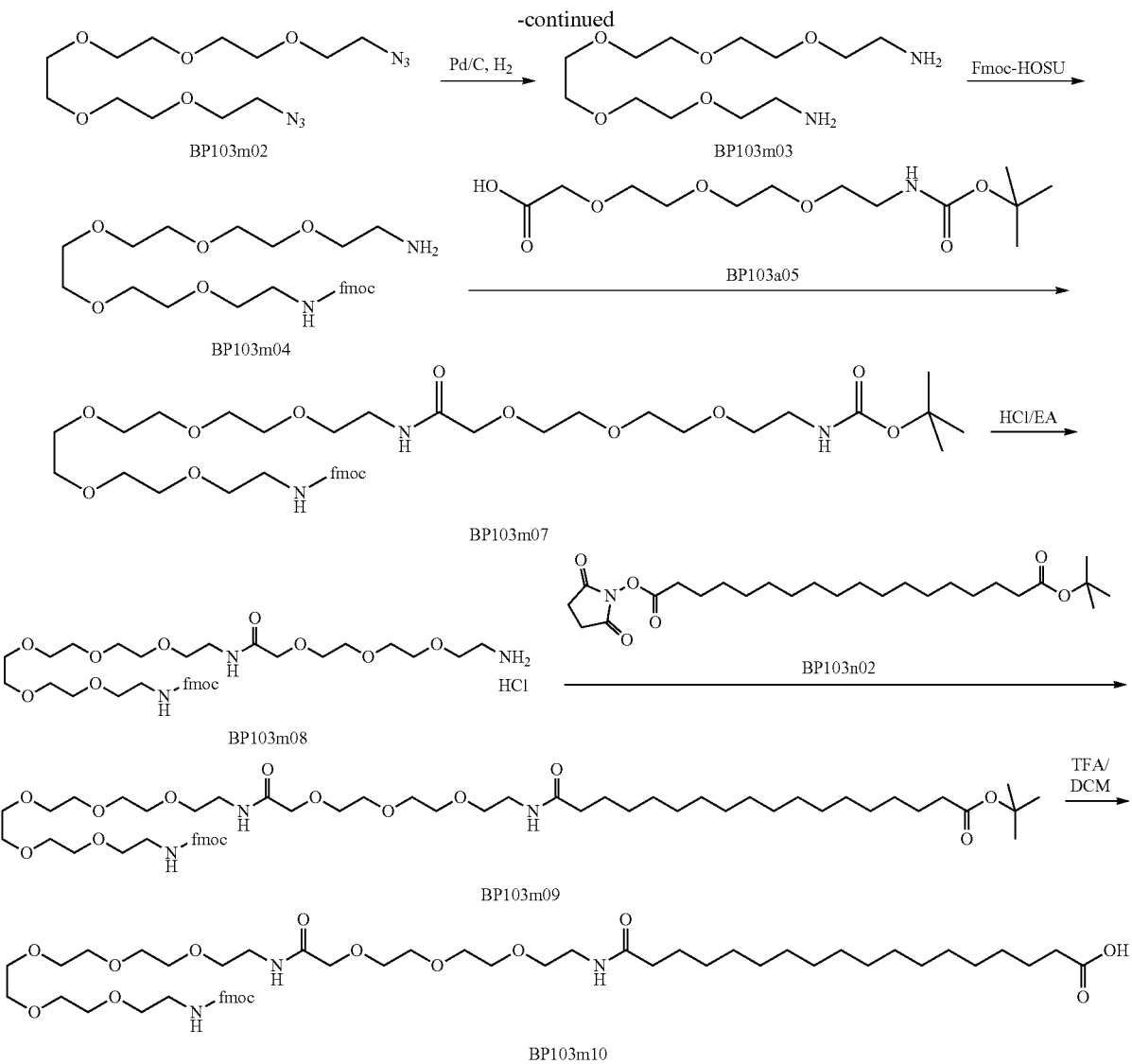

Preparation of BP103m07

To a 100 mL three-necked flask were added compound BP103m04 5.0 g (1.05 eq), 2.9 g BP103a05 (1.0 eq), dichloromethane 50 ml, DIEA 3.8 g (3.0 eq), DEPC 2.4 g (1.5 eq, diethyl cyanophosphonate). After the completion of the reaction under the monitor of TLC, the reaction was washed with 0.1 mol/L HCl/water, sodium bicarbonate, water, and saturated brine, and dried over anhydrous sodium sulfate, and then chromatographed in a column to give 6.3 g BP103m07 as an oil.

Preparation of BP103m08

To a 100 mL flask were added 6.3 g compound BP103m07, 30 ml ethyl acetate, cooled to 0° C. and added 7.0 mol HCl/ethyl acetate. After the completion of the reaction under the monitor of TLC, the organic solvents were evaporated off, slurried with petroleum ether, suction filtrated, and dried to give 5.3 g BP103m08 as an off-white solid.

Preparation of BP103m09

To a 200 mL flask were added 5.0 g BP103m08 (1.0 eq), 50 ml water, 1.2 g NaHCO$_3$ (2.0 eq), and stirred. The solution of 3.2 g compound BP103n02 (1.0 eq) in 50 ml DME (ethylene glycol dimethyl ether) was added dropwise, replenished with 50 ml THF, and stirred overnight. After the completion of the reaction under the monitor of TLC, the organic solvents were evaporated off, adjusted to pH=4 with acetic acid, extracted with ethyl acetate, dried over anhydrous sodium sulfate, and concentrated to give 6.1 g compound BP103m09 as an off-white solid.

Preparation of BP103m10

To a 100 mL flask were added 6.0 g compound BP103m09, 30 ml dichloromethane, 30 ml TFA, and stirred at 20° C. After the completion of the reaction under the monitor of TLC, the organic solvents were evaporated off, slurried with petroleum ether, suction filtrated, and dried to give 4.8 g BP103m10 as an off-white solid.

Preparation of Target Peptide

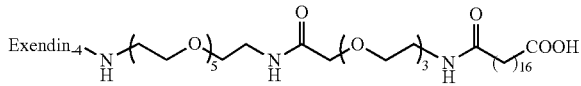

To a 20 ml reaction column were added 1.0 g 2Cl-Trt resin, 296 mg BP103m10, 5 ml dichloromethane, and 300 ul DIEA, into which nitrogen was bubbled for 40 min. 5 ml dichloromethane, 1 ml methanol, and 1 ml DIEA were added and reacted for 20 min, after which they were washed with DMF, producing BP103m06 resin. 20% piperidine/DMF was used for the removal of Fmoc, the reaction was kept for 20 minutes, HOBT/DIC was used as the coupling reagent, and the reactive solvent was DMF. The reaction was monitored by employing the ninhydrin detection method, successively connecting the following protected amino acids onto the resin: Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys (Boc)-OH, Fmoc-Leu-OH, Fmoc-Trp(Boc)-OH, Fmoc-Glu (OtBu)-OH, Fmoc-Ile-OH, Fmoc-Phe-OH, Fmoc-Leu-OH, Fmoc-Arg (Pbf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu) OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Fmoc-His(Trt)-OH, with Fmoc protection finally removed. The pyrolysis of the resin was achieved by employing 82.5% TFA/5% phenol/5% water/ 2.5% EDT/5% thioanisole, and then they were precipitated with ice-cold methyl tert-butyl ether (MTBE), and washed and crude products were purified by reverse HPLC to give 39 mg pure target peptide.

MS (ESI$^+$, m/e): 4932.65[M+H]$^+$

Example 7 Preparation of Compound 7

Compound 7 was prepared with reference to the method of Example 6:

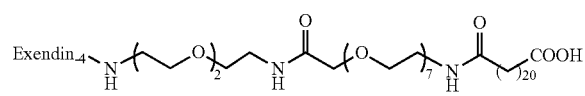

39.6 mg pure target peptide was finally obtained.
MS (ESI$^+$, m/e): 5032.76[M+H]$^+$ Example 8 Preparation of Compound 8

Compound 8 was prepared with reference to the method of Example 6:

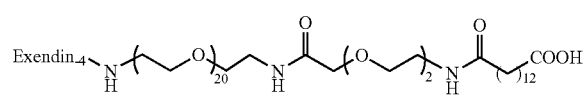

40.2 mg pure target peptide was finally obtained.
MS (ESI$^+$, m/e): 5492.99[M+H]$^+$ Example 9 Preparation of Compound 9

Compound 9 was prepared with reference to the method of Example 6:

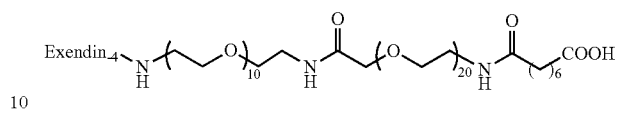

40.7 mg pure target peptide was finally obtained.
MS (ESI$^+$, m/e): 5761.11 [M+H]$^+$ Example 10 Preparation of Compound 10

Compound 10 was prepared with reference to the method of Example 6:

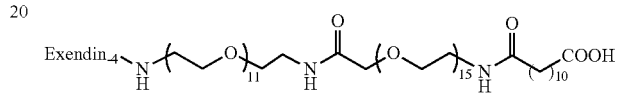

40.7 mg pure target peptide was finally obtained.
MS (ESI$^+$, m/e): 5641.07[M+H]$^+$ Example 11 Preparation of Compound 11

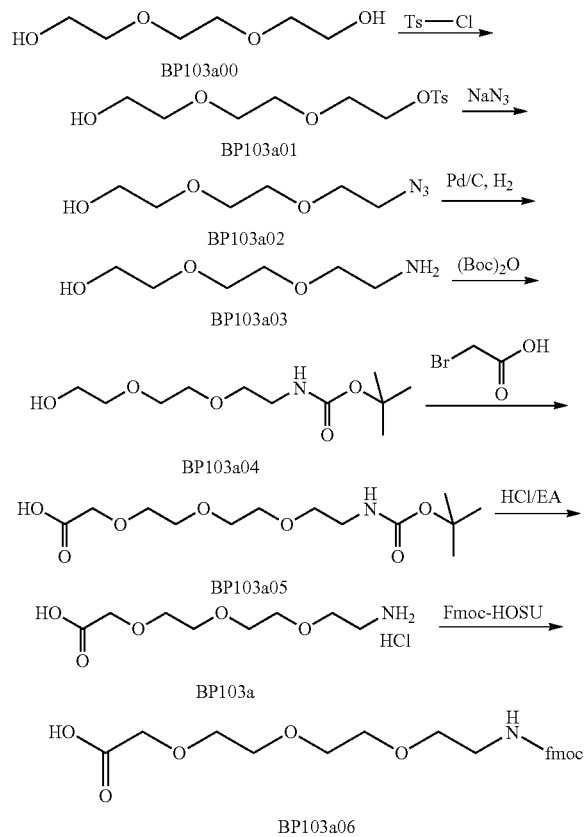

Preparation of BP03a
To a 250 mL three-necked flask were added 18 g compound BP103a05, 100 ml ethyl acetate, stirred to be dissolved and then cooled down to 0° C., with the addition of 150 ml ethyl acetate/HCl (3.5M), keeping the temperature at 0° C. After the completion of the reaction under the monitor of TLC, they was filtered, and the filter cake was washed with TBME to give 10.4 g BP103a as a white solid.

Preparation of BP103a06

To a 200 mL flask were added 5.0 g BP103a (1.0 eq), 50 ml water, 3.5 g NaHCO₃ (2.0 eq), and stirred. A solution of 7.3 g Fmoc-HOSU (1.0 eq) in 50 ml DME (ethylene glycol dimethyl ether) was added dropwise, it was replenished with 50 ml THF, and stirred overnight. After the completion of the reaction under the monitor of TLC, the organic solvents were evaporated off, adjusted to pH=2 with dilute hydrochloric acid, extracted with ethyl acetate, washed with water and saturated brine, dried over anhydrous sodium sulfate, and concentrated to give 7.6 g compound BP103a06 as an off-white solid.

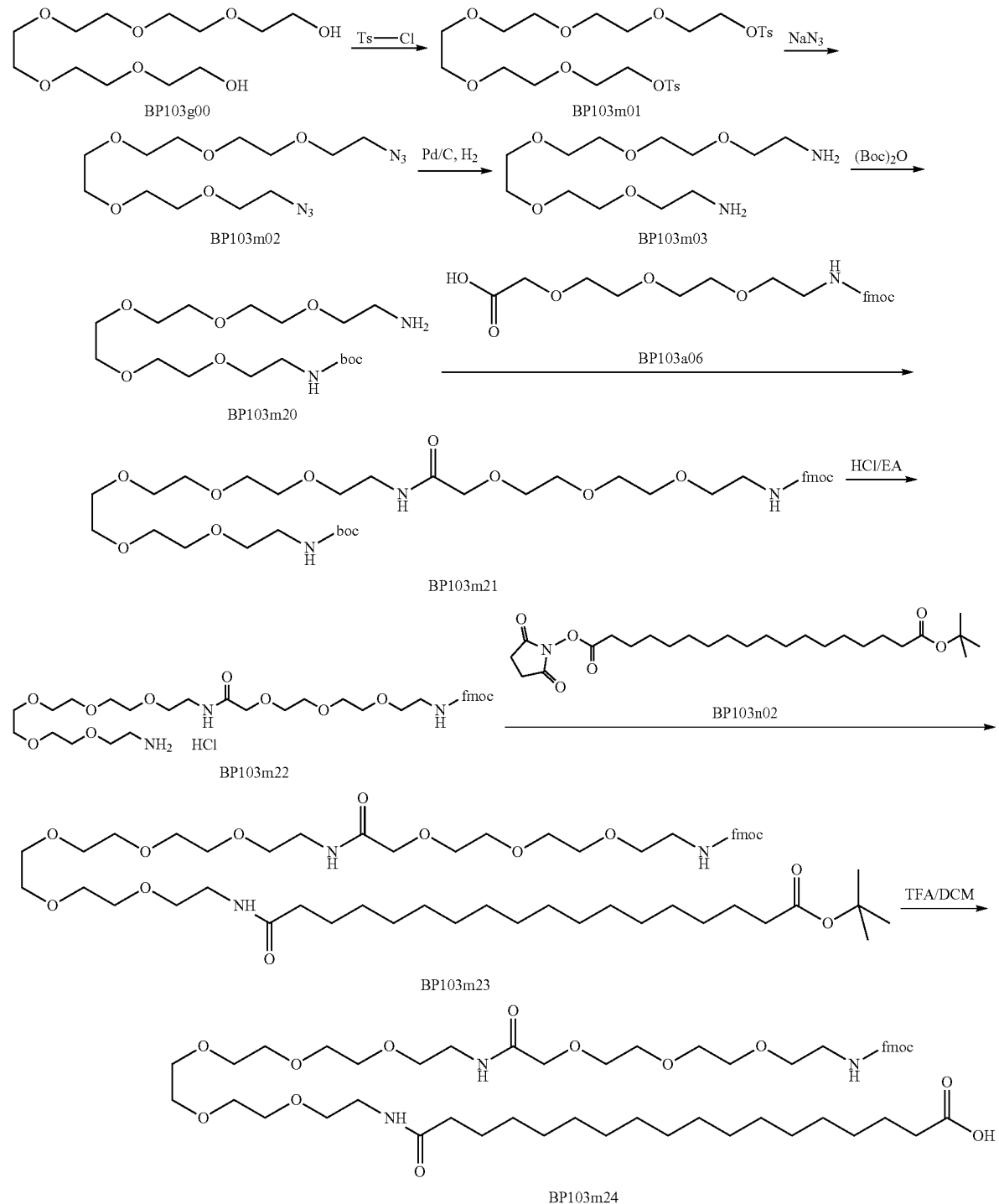

Preparation of BP03m20

To a 500 mL three-necked flask were added compound BP103m03 10.0 g (1.0 eq), dichloromethane 100 ml, (Boc)₂O 7.8 g (1.0 eq), stirred and cooled down to 0° C. 4.6 g DIEA (1.0 eq) was added dropwise, and stirred overnight. After the completion of the reaction under the monitor of TLC, they were washed with water and saturated brine, dried over anhydrous sodium sulfate, and then chromatographed in a column to give 6.2 g BP03m20 as an oil.

Preparation of BP03m21

To a 100 mL three-necked flask were added compound BP103m20 6.2 g (1.05 eq), 6.7 g BP103a06 (1.0 eq), dichloromethane 50 ml, DIEA 6.3 g (3.0 eq), DEPC 4.0 g (1.5 eq). After the completion of the reaction under the monitor of TLC, they were washed with 0.1 mol/L HCl/water, sodium bicarbonate, water, and saturated brine, dried over anhydrous sodium sulfate, and then chromatographed in a column to give 9.5 g BP103m21 as an oil.

Preparation of BP103m22

To a 100 mL flask were added 9.5 g compound BP103m21, 50 ml ethyl acetate, stirred and cooled down to 0° C., with the addition of 50 ml 7.0 mol/L HCl/ethyl acetate. After the completion of the reaction under the monitor of TLC, the organic solvents were evaporated off, slurried with petroleum ether, suction filtrated, and dried to give 8.3 g BP103m22 as an off-white solid.

Preparation of BP103m23

To a 200 mL flask were added 5.0 g BP103m22 (1.0 eq), 50 ml water, 1.2 g NaHCO₃ (2.0 eq), stirred. A solution of 3.2 g compound BP103n02 (1.0 eq) in 50 ml DME (ethylene glycol dimethyl ether) was added dropwise, replenished with 50 ml THF, and stirred overnight. After the completion of the reaction under the monitor of TLC, the organic solvents were evaporated off, adjusted to pH=4 with acetic acid, extracted with ethyl acetate, dried over anhydrous sodium sulfate, and concentrated to give 5.6 g compound BP103m23 as an off-white solid.

Preparation of BP103m24

To a 100 mL flask were added 5.6 g compound BP103m23, 30 ml dichloromethane, 30 ml TFA, and stirred at 20° C. After the completion of the reaction under the monitor of TLC, the organic solvents were evaporated off, slurried with petroleum ether, suction filtrated, and dried to give 4.4 g BP103m24 as an off-white solid.

Preparation of Target Peptide

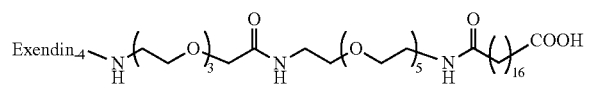

To a 20 ml reaction column were added 1.0 g 2Cl-Trt resin, 296 mg BP103m24, 5 ml dichloromethane, and 300 ul DIEA, into which nitrogen was bubbled for 40 min. 5 ml dichloromethane, 1 ml methanol, 1 ml DIEA were added and reacted for 20 min, after which they were washed with DMF, producing BP103m06 resin. 20% piperidine/DMF was used for the removal of Fmoc, the reaction was kept for 20 minutes, HOBT/DIC was used as the coupling reagent, and the reactive solvent was DMF. The reaction was monitored by employing the ninhydrin detection method, successively connecting the following protected amino acids onto the resin: Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg(Pbf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Fmoc-His(Trt)-OH, with Fmoc protection finally removed. The pyrolysis of the resin was achieved by employing 82.5% TFA/5% phenol/5% water/2.5% EDT/5% thioanisole, and then they were precipitated with ice-cold methyl tert-butyl ether (MTBE), and washed, and crude products were purified by reverse HPLC to give 29 mg pure target peptide.

MS (ESI⁺, m/e): 4932.65[M+H]⁺

Example 12 Preparation of Compound 12

Compound 12 was prepared with reference to the method of Example 11.

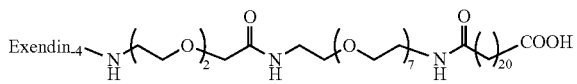

29.1 mg pure target peptide was finally obtained.
MS (ESI⁺, m/e): 5032.76[M+H]⁺

Example 13 Preparation of Compound 13

Compound 13 was prepared with reference to the method of Example 11:

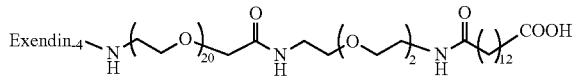

30 mg pure target peptide was finally obtained.
MS (ESI⁺, m/e): 5492.99[M+H]⁺

Example 14 Preparation of Compound 14

Compound 14 was prepared with reference to the method of Example 11:

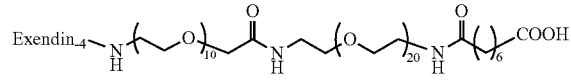

30.2 mg pure target peptide was finally obtained.
MS (ESI⁺, m/e): 5761.11 [M+H]⁺

Example 15 Preparation of Compound 15

Compound 15 was prepared with reference to the method of Example 11:

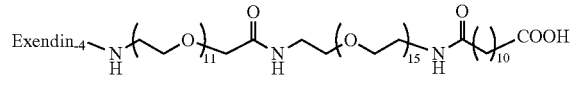

30.4 mg pure target peptide was finally obtained.
MS (ESI⁺, m/e): 5641.07[M+H]⁺

Example 16 Preparation of Compound 16

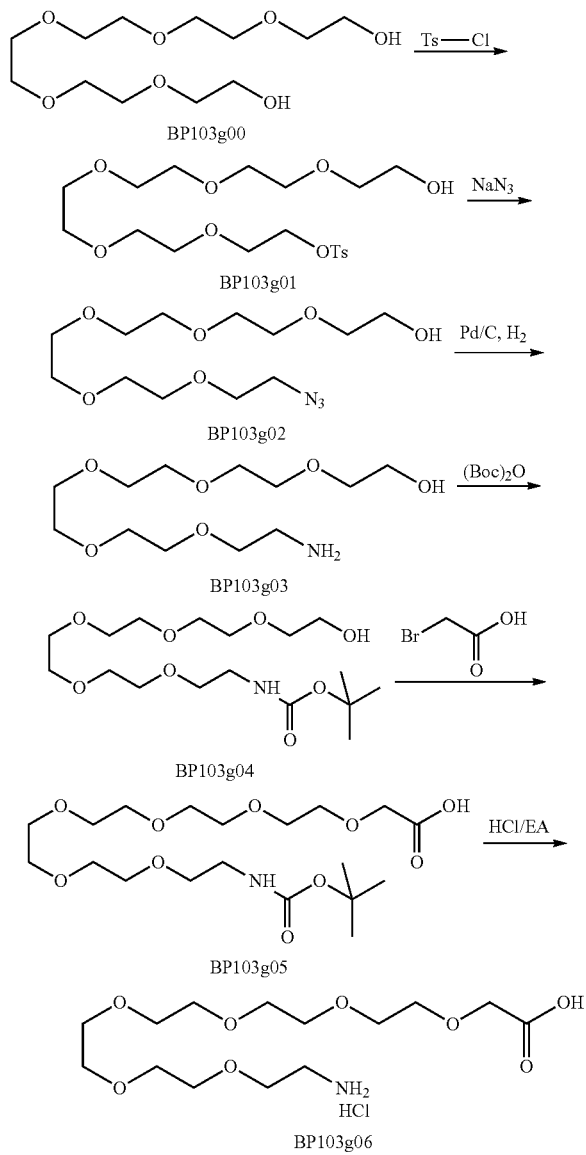

Preparation of Compound BP103g01

Under the protection of nitrogen, to a 500 ml three-necked flask were added 200 mL pyridine 50 g BP103g00 (1.0 eq), stirred and cooled down to 0° C. 35.5 g TsCl (1.0 eq) was added in batches, stirred for 1 h, and then slowly warmed up to room temperature, continuing to stir for 3-4 h. After the completion of the reaction, the reaction liquid was poured into the ice-cold solution of dilute hydrochloric acid, extracted with ethyl acetate. The ethyl acetate layer was washed once with dilute hydrochloric acid, washed with saturated sodium bicarbonate and saturated brine, and dried over anhydrous $Na_2SO_4$. The solvents were evaporated off at reduced pressure, and chromatographed in a silica gel column to give 38 g pure BP103g01.

Preparation of Compound BP103g02

To a 500 mL three-necked flask were added 38 g BP103g01 (1.0 eq) and 190 mL DMSO, stirred evenly, then added $NaN_3$ 11.5 g (2.0 eq), heated to 50° C. and reacted for 3 hours, cooled down to room temperature. The reaction liquid was poured into water, extracted with ethyl acetate for many times. The organic phases were combined, dried over anhydrous sodium sulfate, and concentrated to give 40 g BP103g02 as a colourless liquid.

Preparation of Compound BP103g03

To a 1 L hydrogenation reactor were added BP103g02 70 g, methanol 500 mL, palladium on carbon 8.0 g, stirred, with nitrogen replaced by introducing hydrogen to react for 3-4 h. After the completion of the reaction under the monitor of TLC, the reaction liquid was filtered, and the filtrate was concentrated to give 52 g BP103g03 as an oil.

Preparation of Compound BP103g04

To a 250 mL three-necked flask were added compound BP103g03 10.0 g (1.0 eq), (Boc)$_2$O 15.5 g (2.0 eq), a mixed solution of methanol:triethylamine (9:1) 200 ml, stirred and warmed to reflux, and reacted for 1 h. After the completion of the reaction under the monitor of TLC, methanol triethylamine was evaporated off, and dissolved with water. Dichloromethane was extracted for 3 times. The organic layers were combined and washed once with water, dried over anhydrous sodium sulfate, and concentrated to give 9.0 g BP103g04 as an oil.

Preparation of Compound BP103g05

To a 250 mL three-necked flask were added BP103g04 compound 7.0 g (1.0 eq), toluene and THF 40 ml for each, bromoacetic acid 7.6 g (3.0 eq), stirred, heated to 45~50° C., then added sodium hydroxide 4.4 g, and reacted overnight. After the completion of the reaction under the monitor of TLC, the reaction liquid was evaporated off. The impurities were extracted with water and ethyl acetate, and the aqueous phase was adjusted to pH=3. The aqueous phase was extracted with dichloromethane, and the dichloromethane layers were combined, dried over anhydrous sodium sulfate, and then concentrated to give 4.2 g BP103g05 compound as an oil.

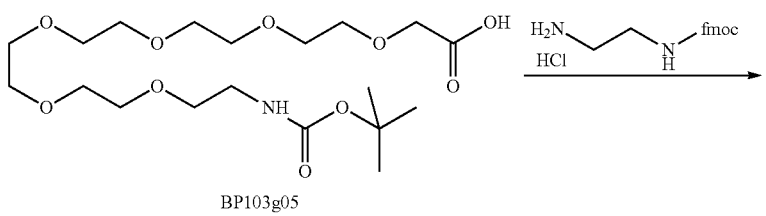

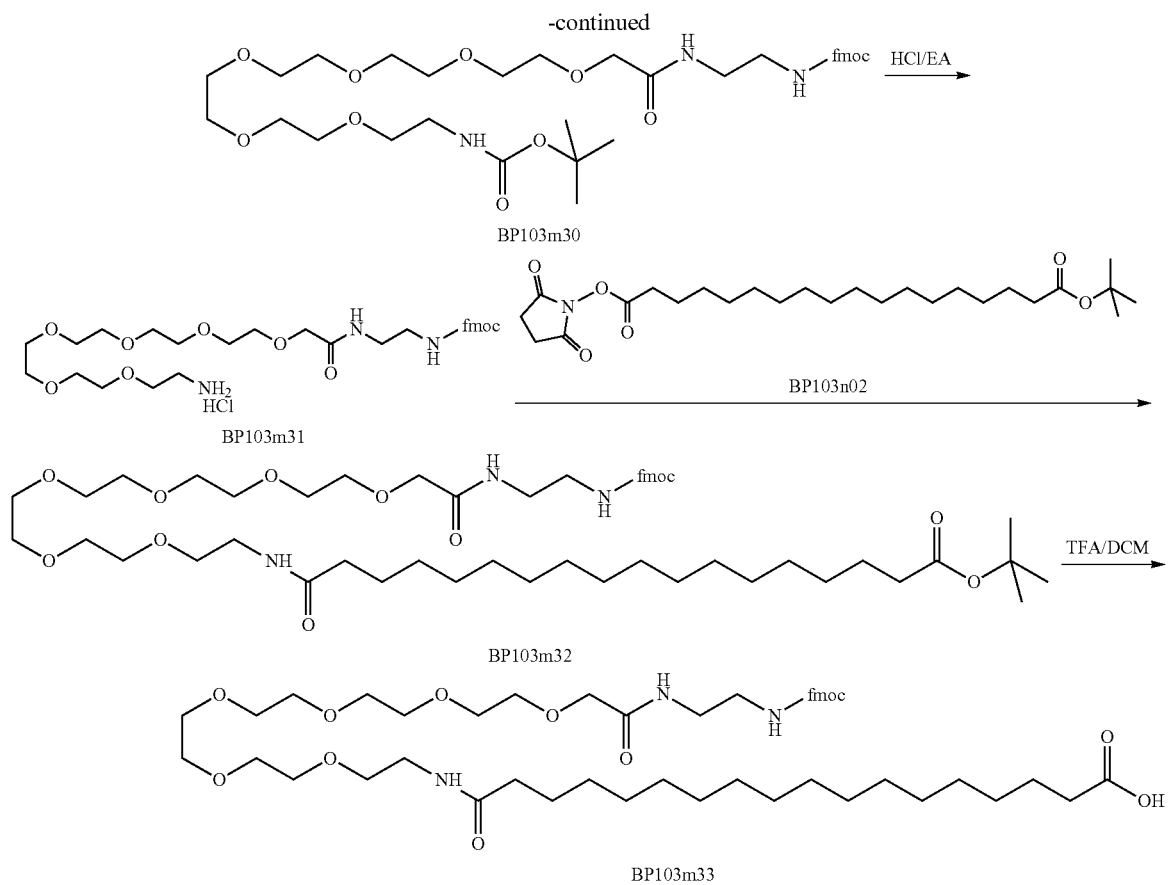

BP103m30

BP103m31

BP103m32

BP103m33

Preparation of BP103m30

To a 100 mL three-necked flask were added compound BP103g05 4.2 g (1.05 eq), 2.9 g Fmoc-ethylenediamine hydrochloride (1.0 eq), dichloromethane 50 ml, DIEA 3.7 g (3.0 eq), DEPC 2.3 g (1.5 eq). After the completion of the reaction under the monitor of TLC, they were washed with 0.1 mol/L HCl/water, sodium bicarbonate, water, and saturated brine, dried over anhydrous sodium sulfate, and then chromatographed in a column to give 5.6 g BP103m21 as an oil.

Preparation of BP103m31

To a 100 mL flask were added 5.6 g compound BP103m30, 30 ml ethyl acetate, stirred and cooled down to 0° C., with the addition of 30 ml 7.0 mol/L HCl/ethyl acetate. After the completion of the reaction under the monitor of TLC, the organic solvents were evaporated off, slurried with petroleum ether, suction filtrated, and dried to give 4.8 g BP103m31 as an off-white solid.

Preparation of BP103m32

To a 200 mL flask were added 4.6 g BP103m31 (1.0 eq), 45 ml water, 1.2 g NaHCO₃ (2.0 eq), and stirred. A solution of 3.4 g compound BP103n02 (1.0 eq) in 45 ml DME (ethylene glycol dimethyl ether) was added dropwise, replenished with 45 ml THF, and stirred overnight. After the completion of the reaction under the monitor of TLC, the organic solvents were evaporated off, adjusted to pH=4 with acetic acid, extracted with ethyl acetate, dried over anhydrous sodium sulfate, and concentrated to give 4.9 g compound BP103m32 as an off-white solid.

Preparation of BP103m33

To a 100 mL flask were added 4.5 g compound BP103m32, 25 ml dichloromethane, 25 ml TFA, and stirred at 20° C. After the completion of the reaction under the monitor of TLC, the organic solvents were evaporated off, slurried with petroleum ether, suction filtrated, and dried to give 3.8 g BP103m33 as an off-white solid.

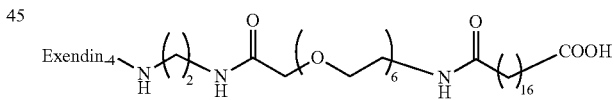

To a 20 ml reaction column were added 1.0 g 2Cl-Trt resin, 270 mg BP103m33, 5 ml dichloromethane, 300 ul DIEA, into which nitrogen was bubbled for 40 min. 5 ml dichloromethane, 1 ml methanol, 1 ml DIEA were added and reacted for 20 min, after which they were washed with DMF, producing BP103m06 resin. 20% piperidine/DMF was used for the removal of Fmoc, the reaction was kept for 20 minutes, HOBT/DIC was used as the coupling reagent, and the reactive solvent was DMF. The reaction was monitored by employing the ninhydrin detection method, successively connecting the following protected amino acids onto the resin: Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg (Pbf)-OH, Fmoc-Val-OH, Fmoc-Ala-OH, Fmoc- Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Fmoc-His(Trt)-OH, with Fmoc protection finally removed. The pyrolysis of the resin was achieved by employing 82.5% TFA/5% phenol/5% water/2.5% EDT/5% thioanisole, and then they were precipitated with ice-cold methyl tert-butyl ether (MTBE), and washed, and crude products were purified by reverse HPLC to give 33 mg pure target peptide.

MS (ESI⁻, m/e): 4844.6[M+H]⁺

Example 17 Preparation of Compound 17

Compound 17 was prepared with reference to the method of Example 16.

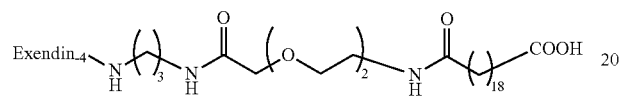

32 mg pure target peptide was finally obtained.
MS (ESI⁺, m/e): 4710.54[M+H]⁺

Example 18 Preparation of Compound 18

Compound 18 was prepared with reference to the method of Example 16.

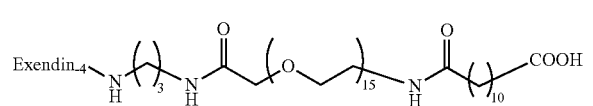

33.5 mg pure target peptide was finally obtained.
MS (ESI⁺, m/e): 5170.77[M+H]⁺

Example 19 Preparation of Compound 19

Compound 19 was prepared with reference to the method of Example 16.

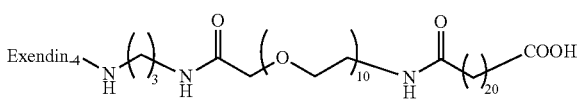

33.1 mg pure target peptide was finally obtained.
MS (ESI⁺, m/e): 5090.82 [M+H]⁺

Example 20 Preparation of Compound 20

Compound 20 was prepared with reference to the method of Example 16.

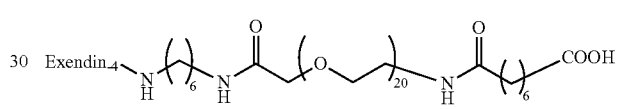

33.1 mg pure target peptide was finally obtained.
MS (ESI⁺, m/e): 5090.82 [M+H]⁺

Example 21 Preparation of Compound 21

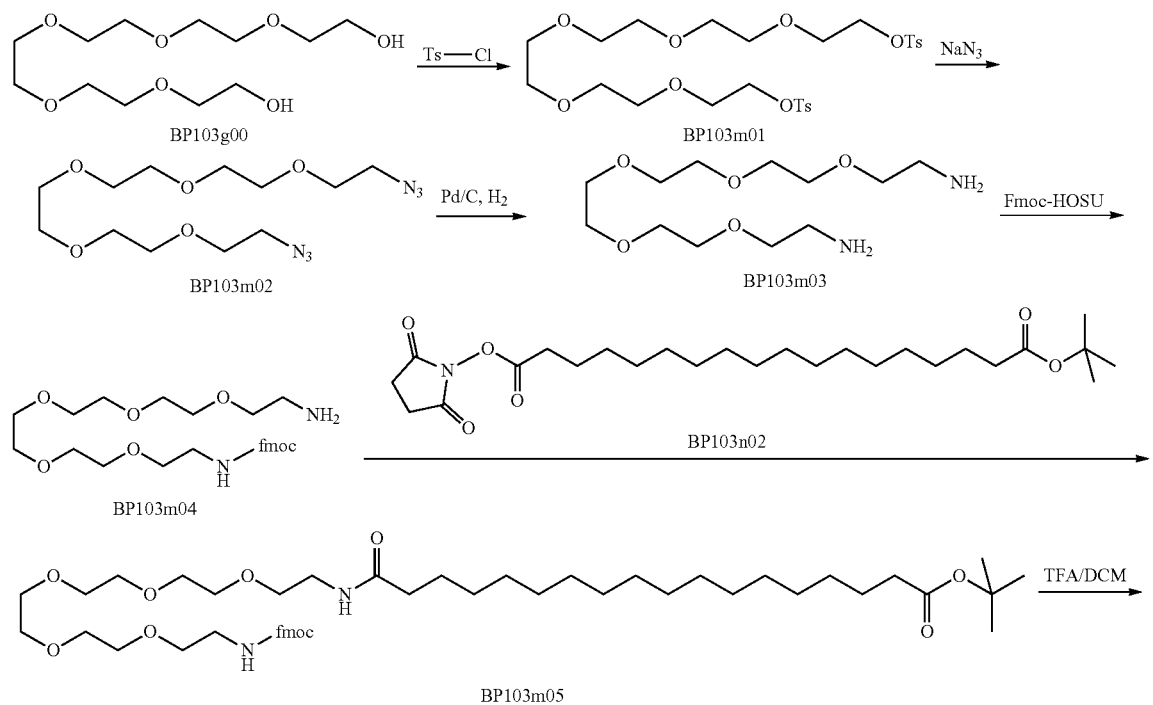

-continued

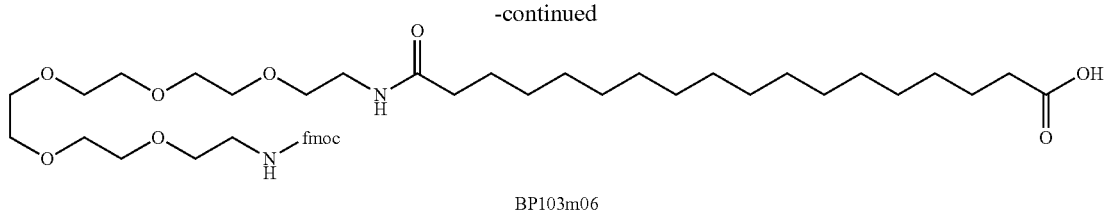

BP103m06

Preparation method of BP103m06 was found in Example 6.

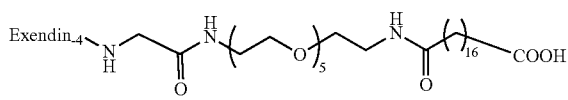

To a 20 ml reaction column were added 1.0 g 2Cl-Trt resin, 240 mg BP103m06, 5 ml dichloromethane, 300 ul DIEA, into which nitrogen was bubbled for 40 min, 5 ml dichloromethane, 1 ml methanol, 1 ml DIEA were added and reacted for 20 min, after which they were washed with DMF, producing BP103m06 resin. 20% piperidine/DMF was used for the removal of Fmoc, the reaction was kept for 20 minutes, HOBT/DIC was used as the coupling reagent, and the reactive solvent was DMF. The reaction was monitored by employing the ninhydrin detection method, successively connecting the following protected amino acids onto the resin: Fmoc-Gly-OH, Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg (Pbf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Fmoc-His(Trt)-OH, with Fmoc protection finally removed. The pyrolysis of the resin was achieved by employing 82.5% TFA/5% phenol/5% water/2.5% EDT/5% thioanisole, and then they were precipitated with ice-cold methyl tert-butyl ether (MTBE), and washed, and crude products were purified by reverse HPLC to give 42 mg pure target peptide.

MS (ESI$^+$, m/e): 4800.56 [M+H]$^+$

Example 22 Preparation of Compound 22

Compound 22 was prepared with reference to the method of Example 21.

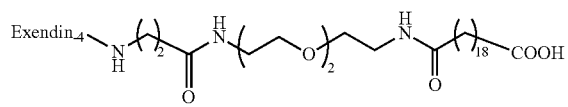

41.7 mg pure target peptide was finally obtained.
MS (ESI$^+$, m/e): 4710.53 [M+H]$^+$ Example 23 Preparation of Compound 23

Compound 23 was prepared with reference to the method of Example 21.

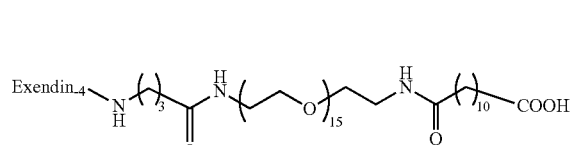

42.5 mg pure target peptide was finally obtained.
MS (ESI$^+$, m/e): 5184.78[M+H]$^+$ Example 24 Preparation of Compound 24

Compound 24 was prepared with reference to the method of Example 21.

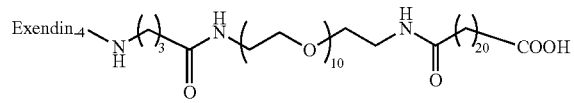

42.1 mg pure target peptide was finally obtained.
MS (ESI$^+$, m/e): 5104.83[M+H]$^+$ Example 25 Preparation of Compound 25

Compound 25 was prepared with reference to the method of Example 21.

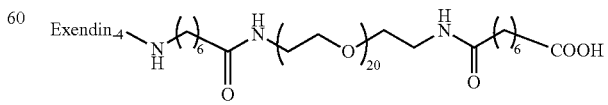

43 mg pure target peptide was finally obtained.
MS (ESI$^+$, m/e): 5390.91[M+H]$^+$ Example 26
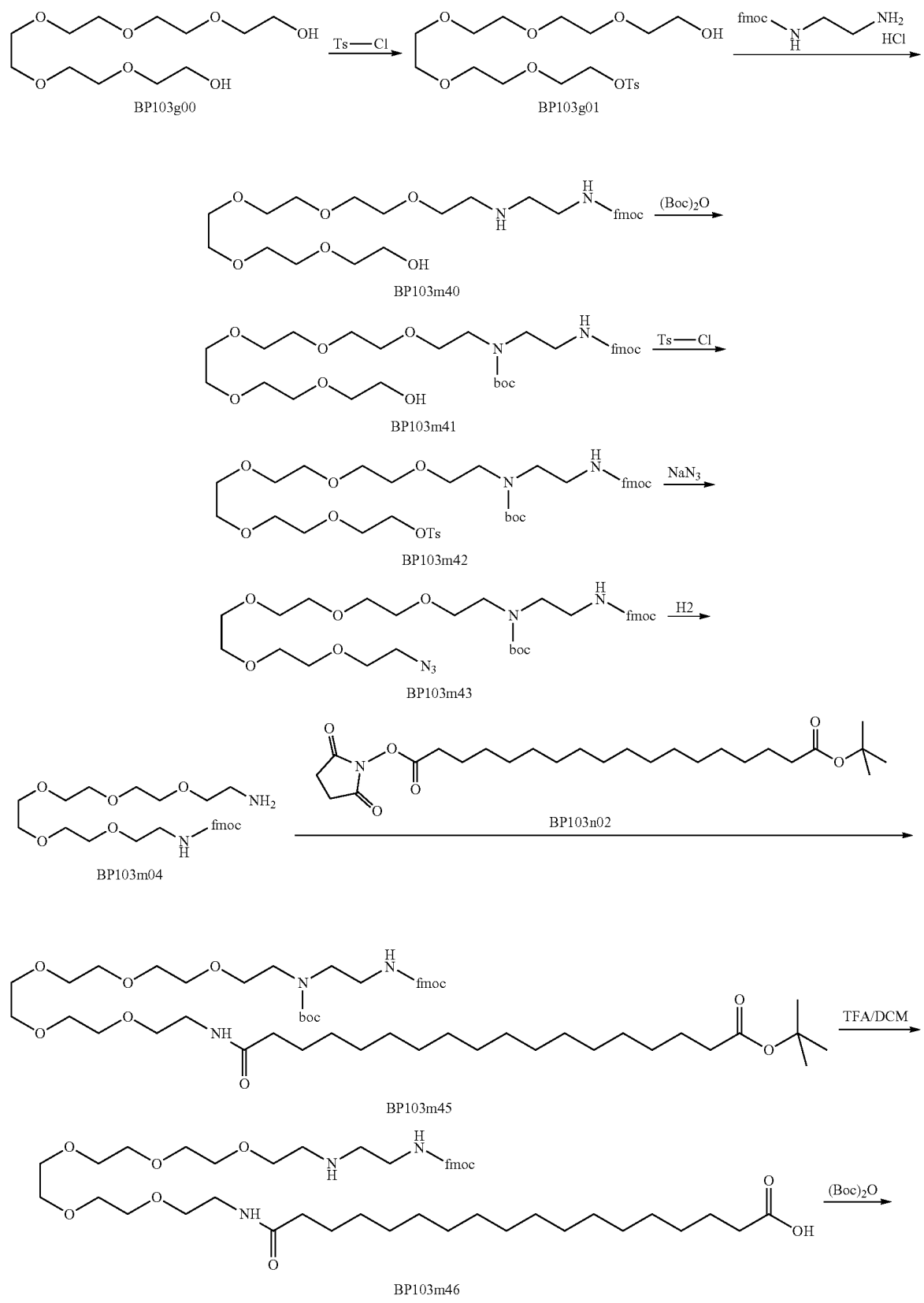

-continued

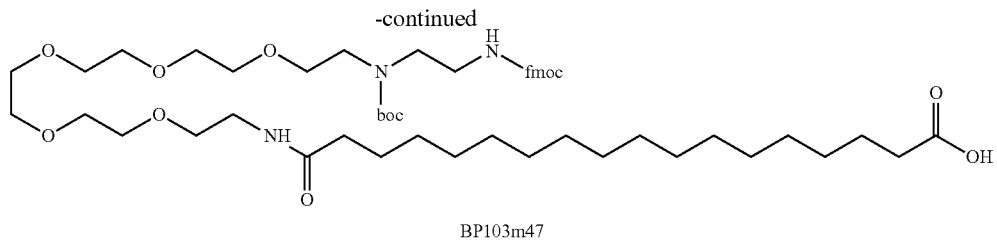

BP103m47

Preparation of BP03m40

To a 500 mL three-necked flask were added compound BP103g01 25.0 g (1.0 eq), acetonitrile 250 ml, Fmoc-ethylenediamine hydrochloride 18.3 g (1.0 eq), stirred and cooled down to 0° C., with the addition of 7.9 g potassium carbonate (1.0 eq). After the completion of the reaction under the monitor of TLC, they were washed with dilute hydrochloric acid and saturated brine, dried over anhydrous sodium sulfate, and then chromatographed in a column to give 25.3 g BP103m40 as an oil.

Preparation of BP03m41

To a 500 mL three-necked flask were added compound BP103m40 25.0 g (1.0 eq), dichloromethane 250 ml, (Boc)$_2$O 19.9 g (2.0 eq), into which 17.7 g DIEA (3.0 eq) was added dropwise. After the completion of the reaction under the monitor of TLC, they were washed with dilute hydrochloric acid, aqueous sodium bicarbonate solution and then saturated brine, dried over anhydrous sodium sulfate, and then chromatographed in a column to give 23.8 g BP103m41 as an oil.

Preparation of BP103m42

Under the protection of nitrogen, to a 1000 ml three-necked flask were added 100 mL pyridine, 23.5 g BP103m41 (1.0 eq), stirred and cooled down to 0° C. 8.3 g TsCl (1.2 eq) was added in batches, stirred for 1 h, and then slowly warmed up to room temperature, continuing to stir for 3-4 h. After the completion of the reaction, most of pyridine was evaporated off, dissolved in ethyl acetate, washed once with dilute hydrochloric acid, washed with saturated sodium bicarbonate and saturated brine, dried over anhydrous Na$_2$SO$_4$, and chromatographed in a silica gel column to give 25.3 g pure BP103m42.

Preparation of BP103m43

To a 1000 mL three-necked flask were added 25.0 g BP103m42 (1.0 eq) and 100 mL DMSO, stirred evenly, then added NaN$_3$ 4.1 g (2.0 eq), heated to 50° C. and reacted for 3 hours, cooled down to room temperature. The reaction liquid was poured into water, extracted with ethyl acetate. The organic phases were combined, dried over anhydrous sodium sulfate, and concentrated to give 22.7 g BP103m43 as a colourless liquid.

Preparation of BP103m44

To a 1 L hydrogenation reactor were added 22.7 g compound BP103m43, methanol 250 mL, palladium on carbon 5.0 g, stirred, with nitrogen replaced by introducing hydrogen to react for 3-4 h. After the completion of the reaction under the monitor of TLC, the reaction liquid was filtered, and the filtrate was concentrated to give 19.6 g BP103m44 as an oil.

Preparation of BP103m45

To a 500 mL flask were added 10.0 g BP103m44 (1.0 eq), 100 ml water, 2.6 g NaHCO$_3$ (2.0 eq), and stirred. A solution of 7.2 g compound BP103n02 (1.0 eq) in 100 ml DME (ethylene glycol dimethyl ether) was added dropwise, replenished with 100 ml THF, and stirred overnight. After the completion of the reaction under the monitor of TLC, the organic solvents were evaporated off, adjusted to pH=4 with acetic acid, extracted with ethyl acetate, dried over anhydrous sodium sulfate, and concentrated to give 13.2 g compound BP103m45 as an off-white solid.

Preparation of BP103m46

To a 100 mL flask were added 13.2 g compound BP103m45, 15 ml dichloromethane, 15 ml TFA, and stirred at 20° C. After the completion of the reaction under the monitor of TLC, the organic solvents were evaporated off, slurried with petroleum ether, suction filtrated, and dried to give 10.5 g BP103m46 as an off-white solid.

Preparation of BP103m47

To a 250 ml three-necked flask were added 10.5 g compound BP103m36 (1.0 eq), 110 ml dichloromethane, 5.4 g (Boc)$_2$O (2.0 eq), into which 4.8 g DIEA (3.0 eq) was added dropwise. After the completion of the reaction under the monitor of TLC, they were washed with dilute hydrochloric acid, aqueous sodium bicarbonate solution, and then saturated brine, dried over anhydrous sodium sulfate, and chromatographed in a column to give 7.9 g BP103m47 as an off-white solid.

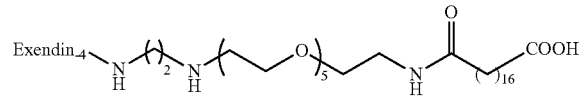

To a 20 ml reaction column were added 1.0 g 2Cl-Trt resin, 283 mg BP103m47, 5 ml dichloromethane, and 300 ul DIEA, into which nitrogen was bubbled for 40 min. 5 ml dichloromethane, 1 ml methanol, and 1 ml DIEA were added and reacted for 20 min, after which they were washed with DMF, producing BP103m06 resin. 20% piperidine/DMF was used for the removal of Fmoc, the reaction was kept for 20 minutes, HOBT/DIC was used as the coupling reagent, and the reactive solvent was DMF. The reaction was monitored by employing the ninhydrin detection method, successively connecting the following protected amino acids onto the resin: Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg (Pbf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Fmoc-His(Trt)-OH, with Fmoc protection finally removed. The pyrolysis of the resin was achieved by employing 82.5% TFA/5% phenol/5% water/

2.5% EDT/5% thioanisole, and then they were precipitated with ice-cold methyl tert-butyl ether (MTBE), and washed, and crude products were purified by reverse HPLC to give 41 mg pure target peptide.
MS (ESI⁺, m/e): 4771.57[M+H]⁺

Example 27 Preparation of Compound 27

Compound 27 was prepared with reference to the method of Example 26.

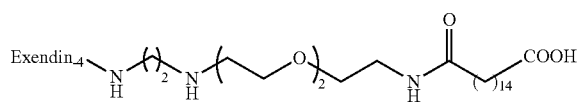

40.5 mg pure target peptide was finally obtained.
MS (ESI⁺, m/e): 4611.44[M+H]⁺

Example 28 Preparation of Compound 28

Compound 28 was prepared with reference to the method of Example 26.

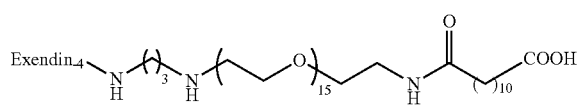

41.6 mg pure target peptide was finally obtained.
MS (ESI⁺, m/e): 5141.77[M+H]⁺

Example 29 Preparation of Compound 29

Compound 29 was prepared with reference to the method of Example 26.

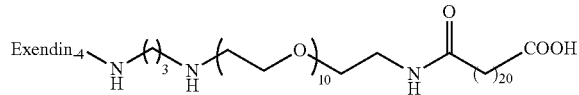

41.2 mg pure target peptide was finally obtained.
MS (ESI⁺, m/e): 5061.82[M+H]⁺

Example 30 Preparation of Compound 30

Compound 30 was prepared with reference to the method of Example 26.

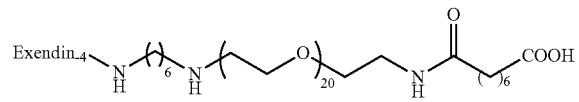

42.3 mg pure target peptide was finally obtained.
MS (ESI⁺, m/e): 5347.9[M+H]⁺

Example 31 Preparation of Compound 31

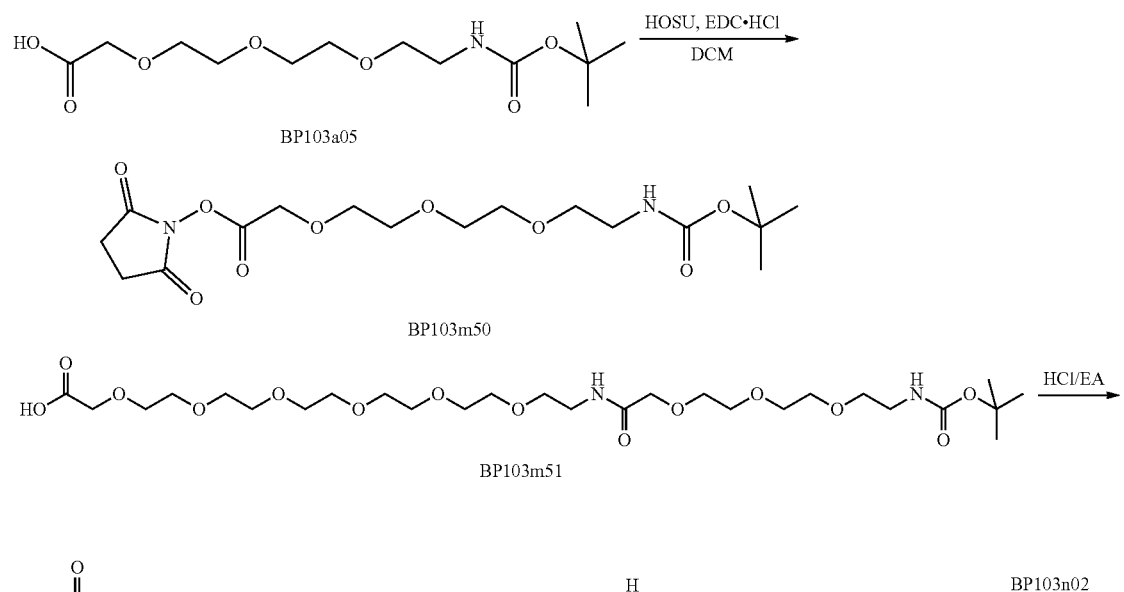

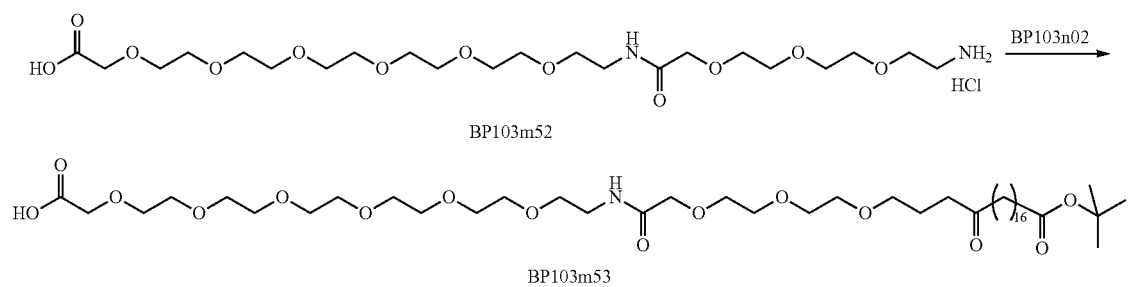

Preparation of BP103m50

To a 100 mL three-necked flask were added 286 mg N-hydroxy succinimide (HOSU), 0.50 g BP103a05 and 5 ml dichloromethane, into which 477 mg EDC.HCl was added and reacted at room temperature for 2 h. After the completion of the reaction under the monitor of TLC, they were diluted with dichloromethane, and then washed with 50 mmol/L aqueous solution of potassium dihydrogen phosphate at pH=6.0 for 2 times, washed with saturated brine, dried over anhydrous sodium sulfate, and concentrated to give 0.72 g compound BP103m50 as an oil.

Preparation of BP103m51

To a 100 mL flask were added 0.62 g compound BP103g06 (1.0 eq), 10 ml water, 0.27 g NaHCO₃ (2.0 eq), and stirred. A solution of 0.66 g compound BP103m50 in 10 ml DME (ethylene glycol dimethyl ether) was added dropwise, replenished with 5 ml THF, and stirred overnight. After the completion of the reaction under the monitor of TLC, the organic solvents were evaporated off, adjusted to pH=4 with dilute hydrochloric acid, extracted with dichloromethane, dried over anhydrous sodium sulfate, and concentrated to give 0.71 g compound BP103m51 as an oil.

Preparation of BP103m52

To a 100 mL flask were added 0.71 g compound BP103m51 and 5 ml ethyl acetate, after being dissolved, they were cooled down to 0° C., into which 5 ml HCl/ethyl acetate (7 mol/L) was added, keeping the temperature at 0° C. After the completion of the reaction under the monitor of TLC, they were concentrated to give 0.71 g BP103m52 as an oil.

Preparation of BP103m53

To a 100 mL flask were added 640 mg compound BP103m52 (1.0 eq), 15 ml water, 190 mg NaHCO₃ (2.0 eq), and stirred. A solution of 528 mg compound BP103n02 in 15 ml DME (ethylene glycol dimethyl ether) was added dropwise, replenished with 15 ml THF, and stirred overnight. After the completion of the reaction under the monitor of TLC, the organic solvents were evaporated off, adjusted to pH=6 with acetic acid, extracted with dichloromethane, dried over anhydrous sodium sulfate, and concentrated to give 0.65 g compound BP103m53 as an oil.

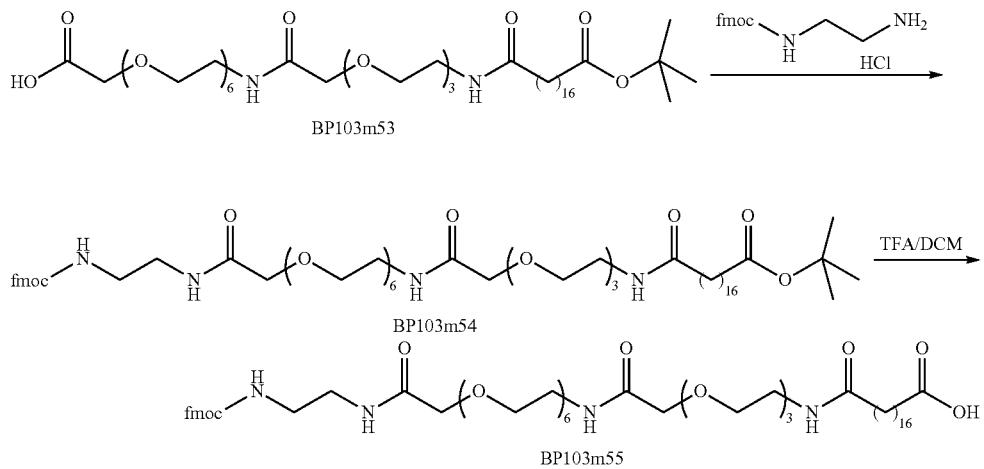

Preparation of BP03m54

To a 100 mL three-necked flask were added compound BP103m53 3.0 g (1.0 eq), 1.1 g Fmoc-ethylenediamine hydrochloride (1.05 eq), dichloromethane 30 ml, DIEA 1.3 g (3.0 eq), and DEPC 0.8 g (1.5 eq). After the completion of the reaction under the monitor of TLC, they were washed with 0.1 mol/L HCl/water, sodium bicarbonate, water, and saturated brine, dried over anhydrous sodium sulfate, and then chromatographed in a column to give 2.9 g BP103m54 as an oil.

Preparation of BP103m55

To a 100 mL flask were added 2.9 g compound BP103m54, 15 ml dichloromethane, 15 ml TFA, and stirred at 20° C. After the completion of the reaction under the monitor of TLC, the organic solvents were evaporated off, slurried with petroleum ether, suction filtrated, and dried to give 2.5 g BP103m55 as an off-white solid.

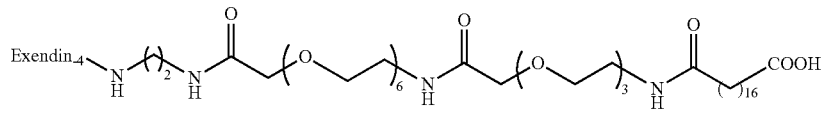

To a 20 ml reaction column were added 1.0 g 2Cl-Trt resin, 344 mg BP103m55, 5 ml dichloromethane, and 300 ul DIEA, into which nitrogen was bubbled for 40 min. 5 ml dichloromethane, 1 ml methanol, and 1 ml DIEA were added and reacted for 20 min, after which they were washed with DMF, producing BP103m06 resin. 20% piperidine/DMF was used for the removal of Fmoc, the reaction was kept for 20 minutes, HOBT/DIC was used as the coupling reagent, and the reactive solvent was DMF. The reaction was monitored by employing the ninhydrin detection method, successively connecting the following protected amino acids onto the resin: Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg (Pbf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Fmoc-His(Trt)-OH, with Fmoc protection finally removed. The pyrolysis of the resin was achieved by employing 82.5% TFA/5% phenol/5% water/2.5% EDT/5% thioanisole, and then they were precipitated with ice-cold methyl tert-butyl ether (MTBE), and washed, and crude products were purified by reverse HPLC to give 46 mg pure target peptide.

MS (ESI$^+$, m/e): 5033.72[M+H]$^+$

Example 32 Preparation of Compound 32

Compound 32 was prepared with reference to the method of Example 31.

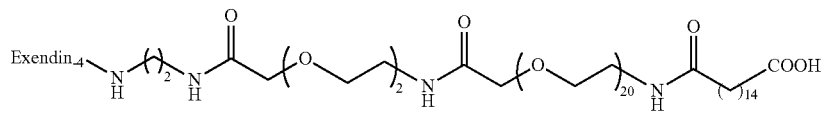

46.8 mg pure target peptide was finally obtained.
MS (ESI$^+$, m/e): 5578.07[M+H]$^+$ Example 33 Preparation of Compound 33

Compound 33 was prepared with reference to the method of Example 31.

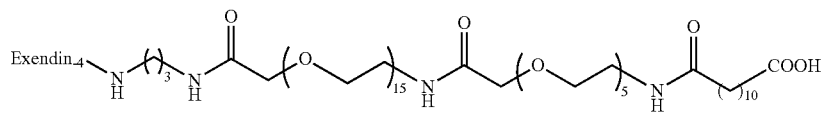

46.4 mg pure target peptide was finally obtained.
MS (ESI$^+$, m/e): 5447.95[M+H]$^+$ Example 34 Preparation of Compound 34

Compound 34 was prepared with reference to the method of Example 31.

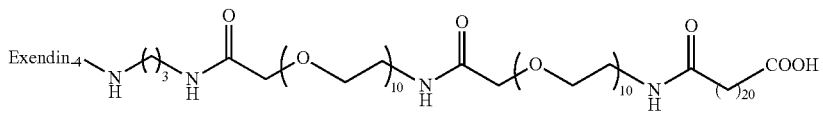

46.5 mg pure target peptide was finally obtained.
MS (ESI$^+$, m/e): 5588.15 [M+H]$^+$ Example 35 Preparation of Compound 35

Compound 35 was prepared with reference to the method of Example 31.

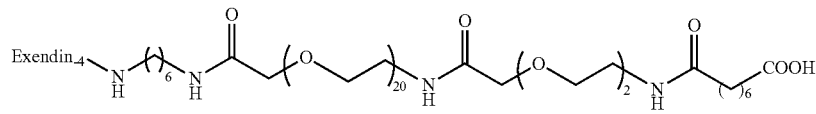

46 mg pure target peptide was finally obtained.
MS (ESI$^+$, m/e): 5521.99 [M+H]$^+$ Example 36 Preparation of Compound 36

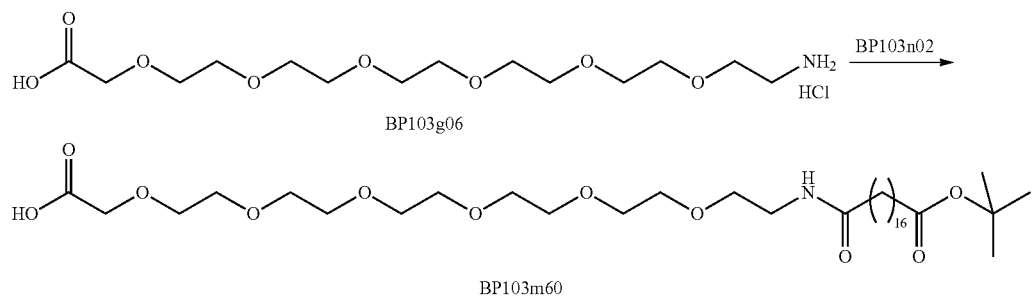

Preparation of BP103m60

To a 500 mL flask were added 10.0 g BP103g06 (1.0 eq), 100 ml water, 4.5 g NaHCO$_3$ (2.0 eq), and stirred. A solution of 12.4 g compound BP103n02 (1.0 eq) in 100 ml DME (ethylene glycol dimethyl ether) was added dropwise, replenished with 100 ml THF, and stirred overnight. After the completion of the reaction under the monitor of TLC, the organic solvents were evaporated off, adjusted to pH=4 with acetic acid, extracted with ethyl acetate, dried over anhydrous sodium sulfate, and concentrated to give 15.2 g compound BP103m60 as an off-white solid.

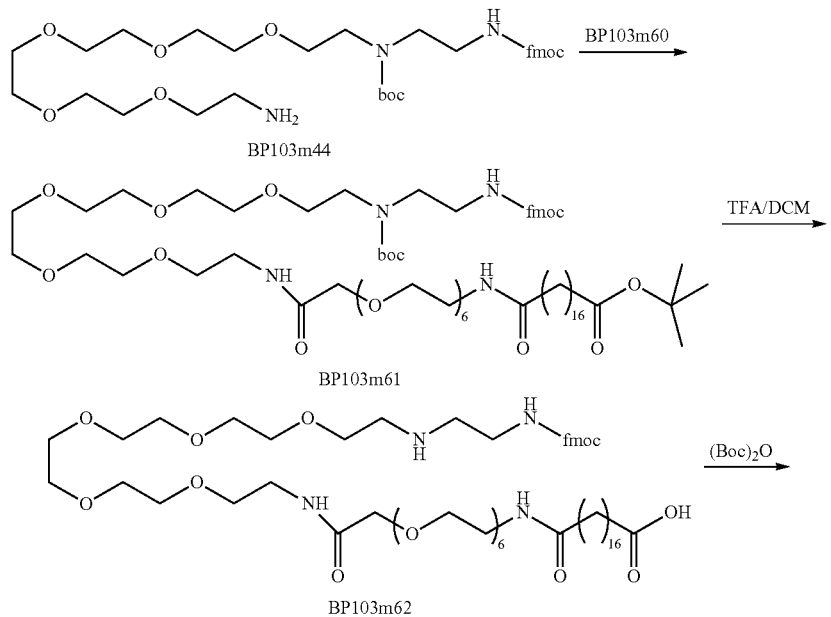

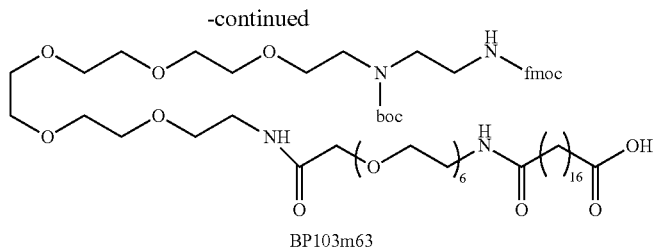

BP103m63

Preparation of BP03m61

To a 100 mL three-necked flask were added compound BP103m44 3.0 g (1.05 eq), 3.1 g (1.0 eq) BP103m60, dichloromethane 30 ml, DIEA 1.7 g (3.0 eq), DEPC 1.1 g (1.5 eq). After the completion of the reaction under the monitor of TLC, they were washed with 0.1 mol/L HCl/water, sodium bicarbonate, water, and saturated brine, dried over anhydrous sodium sulfate, and then chromatographed in a column to give 4.1 g BP103m61 as an oil.

Preparation of BP103m62

To a 100 mL flask were added 4.1 g compound BP103m61, 20 ml dichloromethane, 20 ml TFA, and stirred at 20° C. After the completion of the reaction under the monitor of TLC, the organic solvents were evaporated off, slurried with petroleum ether, suction filtrated, and dried to give 3.5 g BP103m62 as an off-white solid.

Preparation of BP103m63

To a 250 ml three-necked flask were added 3.5 g compound BP103m62 (1.0 eq), 50 ml dichloromethane, and 1.2 g (Boc)₂O (2.0 eq), into which 1.1 g DIEA (3.0 eq) was added dropwise. After the completion of the reaction under the monitor of TLC, they were washed with dilute hydrochloric acid, aqueous sodium bicarbonate solution, and then saturated brine, dried over anhydrous sodium sulfate, and chromatographed in a column to give 2.6 g BP103m63 as an off-white solid.

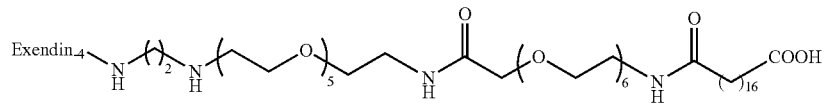

To a 20 ml reaction column were added 1.0 g 2Cl-Trt resin, 408 mg BP103m63, 5 ml dichloromethane, 300 ul DIEA, into which nitrogen was bubbled for 40 min. 5 ml dichloromethane, 1 ml methanol, and 1 ml DIEA were added and reacted for 20 min, after which they were washed with DMF, producing BP103m06 resin. 20% piperidine/DMF was used for the removal of Fmoc, the reaction was kept for 20 minutes, HOBT/DIC was used as the coupling reagent, and the reactive solvent was DMF. The reaction was monitored by employing the ninhydrin detection method, successively connecting the following protected amino acids onto the resin: Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg (Pbf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu) OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Fmoc-His(Trt)-OH, with Fmoc protection finally removed. The pyrolysis of the resin was achieved by employing 82.5% TFA/5% phenol/5% water/2.5% EDT/5% thioanisole, and then they were precipitated with ice-cold methyl tert-butyl ether (MTBE), and washed, and crude products were purified by reverse HPLC to give 55 mg pure target peptide.

MS (ESI⁺, m/e): 5107.81[M+H]⁺

Example 37 Preparation of Compound 37

Compound 37 was prepared with reference to the method of Example 36.

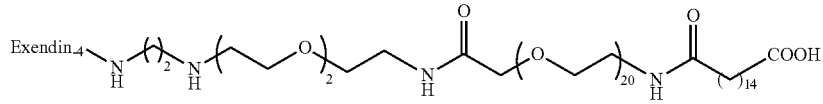

55.7 mg pure target peptide was finally obtained.
MS (ESI$^+$, m/e): 5564.1 [M+H]$^+$

Example 38 Preparation of Compound 38

Compound 38 was prepared with reference to the method of Example 36.

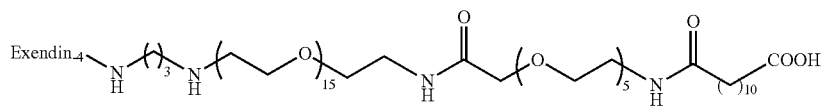

55 mg pure target peptide was finally obtained.
MS (ESI$^+$, m/e): 5433.98 [M+H]$^+$

Example 39 Preparation of Compound 39

Compound 39 was prepared with reference to the method of Example 36.

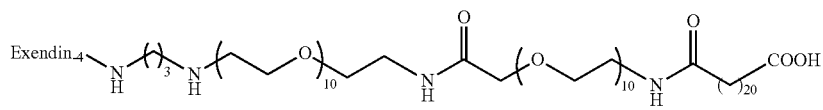

55.2 mg pure target peptide was finally obtained.
MS (ESI$^+$, m/e): 5574.18 [M+H]$^+$

Example 40 Preparation of Compound 40

Compound 40 was prepared with reference to the method of Example 36.

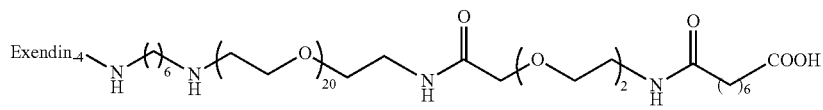

55.3 mg pure target peptide was finally obtained.
MS (ESI$^+$, m/e): 5508.02[M+H]$^+$

Example 41 Preparation of Compound 41

Preparation of Exendin-4(1-39)-Lys40(Alloc)-NH$_2$

The solid phase peptides of target peptides were synthesized by employing the solid phase synthesis of Fmoc process, using Fmoc-Rink MBHA Amide resin, in which 20% piperidine/DMF was used to remove Fmoc, HOBT/DIC was used as the coupling reagent, and the reactive solvent was DMF. The reaction was monitored by employing the ninhydrin detection method, successively connecting the following protected amino acids onto the Rink MBHA Amide resin: Fmoc-Lys(Alloc)-OH, Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg (Pbf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Fmoc-His(Trt)-OH, (BOC)$_2$O (using DIEA, dichloromethane). They were washed with DMF, methanol, and dichloromethane, and then dried to give 12.1 g Exendin-4(1-39)-Lys40(Alloc)-NH$_2$ resin.

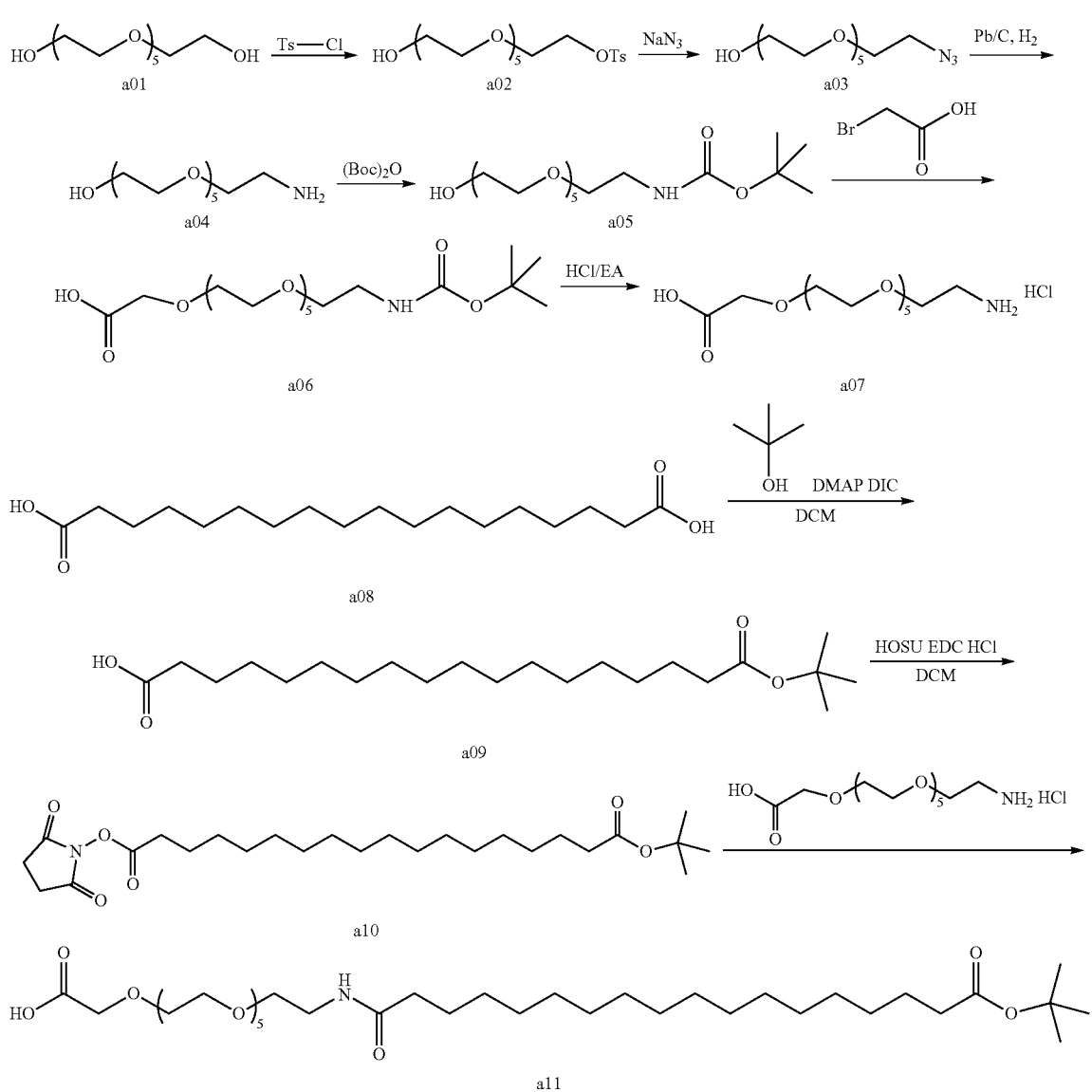

Preparation of Compound a02

Under the protection of nitrogen, to a 500 ml three-necked flask were added 200 mL pyridine, 50 g a01 (1.0 eq), stirred and cooled down to 0° C., into which 35.5 g TsCl (1.0 eq) was added in batches, stirred for 1 h, and then slowly warmed up to room temperature, continuing to stir for 3-4 h. After the completion of the reaction, the reaction liquid was poured into the ice-cold solution of dilute hydrochloric acid, with a solid being generated, which was extracted with ethyl acetate. The ethyl acetate layer was washed once with dilute hydrochloric acid, washed with saturated sodium bicarbonate and saturated brine, and dried over anhydrous Na$_2$SO$_4$. The solvents were evaporated off at reduced pressure, and chromatographed in a silica gel column to give 38 g pure a02.

Preparation of Compound a03

To a 500 mL three-necked flask were added 38 g a (1.0 eq) and 190 mL DMSO, stirred evenly, then added NaN$_3$ 11.5 g (2.0 eq), heated to 50° C. and reacted for 3 hours, cooled down to room temperature. The reaction liquid was poured into water, extracted with ethyl acetate for many times. The organic phases were combined, dried over anhydrous sodium sulfate, and concentrated to give 40 g a03 as a colourless liquid.

Preparation of Compound a04

To a 1 L hydrogenation reactor were added a03 70 g, methanol 500 mL, palladium on carbon 8.0 g, and stirred, with nitrogen replaced by introducing hydrogen to react for 3-4 h. After the completion of the reaction under the monitor of TLC, the reaction liquid was filtered, and the filtrate was concentrated to give 52 g a04 as an oil.

Preparation of Compound a05

To a 250 mL three-necked flask were added compound a04 10.0 g (1.0 eq), (Boc)$_2$O 15.5 g (2.0 eq), a mixed solution of methanol:triethylamine (9:1) 200 ml, stirred, warmed to reflux, and reacted for 1 h. After the completion of the reaction under the monitor of TLC, methanol triethylamine was evaporated off, and they were dissolved in water, and extracted with dichloromethane for 3 times. The organic layers were combined and washed once with water, dried over anhydrous sodium sulfate, and concentrated to give 9.0 g a05 as an oil.

Preparation of Compound a06

To a 250 mL three-necked flask were added a05 compound 7.0 g (1.0 eq), toluene and THF 40 ml for each, bromoacetic acid 7.6 g (3.0 eq), stirred, and heated to 45-50° C. into which 4.4 g sodium hydroxide was then added, and reacted overnight. After the completion of the reaction under the monitor of TLC, the reaction liquid was evaporated off, the impurities were extracted with water and ethyl acetate, and the aqueous phase was adjusted to pH=3. The aqueous phase was extracted with dichloromethane, and the dichloromethane layers were combined, dried over anhydrous sodium sulfate, and then concentrated to give 4.2 g a06 compound as an oil.

Preparation of Compound a07

To a 250 mL single-neck flask were added compound a06 4.0 g and 20 ml ethyl acetate, after being dissolved, they were cooled down to 0° C., into which was added 20 ml HCl/ethyl acetate (7 mol/L). After the completion of the reaction under the monitor of TLC, they were concentrated to give 4.2 g a07 as an oil.

Preparation of Compound a09

To a 50 mL three-necked flask were added 1.0 g compound a08 (1.0 eq), 10 ml dichloromethane, 10 ml tert-butanol, 0.40 g DIC (1.0 eq), 0.39 g DMAP (1.0 eq), and stirred overnight at room temperature. After the completion of the reaction under the monitor of TLC, they were diluted with ether, then washed with water for 3 times and washed with saturated brine, dried over anhydrous sodium sulfate, and chromatographed in a column to give 0.4 g a09 as a foamy powder.

Preparation of Compound a10

To a 100 mL three-necked flask were added 0.95 g N-hydroxy succinimide (HOSU), 2.0 g compound a09 and 15 ml dichloromethane, into which 1.58 g EDC-HCl was added and reacted for 2 h at room temperature. After the completion of the reaction under the monitor of TLC, they were diluted with dichloromethane, then washed with 50 mmol/L aqueous solution of potassium dihydrogen phosphate at pH=6.0 for 2 times, and washed with saturated brine, dried over anhydrous sodium sulfate, and concentrated to give 2.6 g compound a10 as an oil.

Preparation of Compound a11

To a 100 mL flask were added 1.28 g compound a07 (1.0 eq), 20 ml water, 1.16 g NaHCO$_3$ (4.0 eq), and stirred. A solution of 1.75 g compound a10 in 20 ml DME (ethylene glycol dimethyl ether) was added dropwise, replenished with 20 ml THF, and stirred overnight. After the completion of the reaction under the monitor of TLC, the organic solvents were evaporated off, adjusted to pH=6 with acetic acid, extracted with ethyl acetate, dried over anhydrous sodium sulfate, and concentrated to give an off-white solid, which was chromatographed in a column to give 0.95 g compound a11.

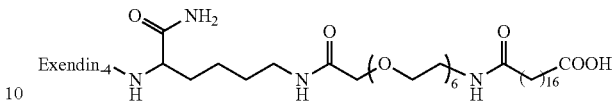

1.5 g Exendin-4(1-39)-Lys40-NH$_2$ resin was swelled in DMF, into which was then added 3 eq solution of Pd(PPh$_3$)$_4$ in CHCl$_3$:AcOH:NMM (18:1:0.5). They were reacted for 2 h, then washed with chloroform (6 times, 20 ml chloroform for each time), washed with 20% solution of HOAc in dichloromethane (6 times, 20 ml 20% solution of HOAc in dichloromethane for each time), washed with dichloromethane (6 times, 20 ml dichloromethane for each time) and washed with DMF (6 times, 20 ml DMF for each time). When it was detected with ninhydrin as positive, 5 ml DMF, 415 mg compound a11, 150 mg HOAT, and 150 ul DIC were added and reacted for 4 h; and when it was detected with ninhydrin as negative, indicting that the side chain a11 has connected onto Exendin-4(1-39)-Lys40-NH$_2$ resin. The pyrolysis of the resin was carried out by employing 82.5% TFA/5% phenol/5% water/2.5% EDT/5% thioanisole, and then they were precipitated with ice-cold methyl tert-butyl ether (MTBE), and washed. Crude products were purified by HPLC to give 43 mg target compound.

MS (ESI$^+$, m/e): 4932.56 [M+H]$^+$

Example 42 Preparation of Compound 42

Compound 42 was prepared with reference to the method of Example 41.

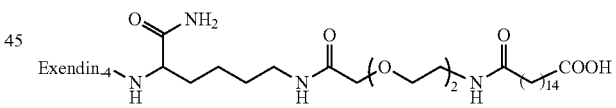

41 mg pure target peptide was finally obtained.

MS (ESI$^+$, m/e): 4725.38[M+H]$^+$

Example 43 Preparation of Compound 43

Compound 43 was prepared with reference to the method of Example 41.

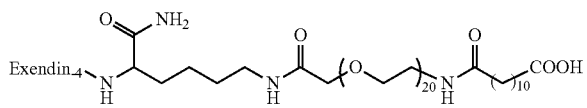

41.5 mg pure target peptide was finally obtained.

MS (ESI$^+$, m/e): 5461.93[M+H]$^+$

Example 44 Preparation of Compound 44

Compound 44 was prepared with reference to the method of Example 41.

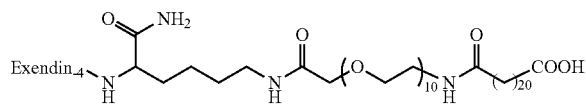

43 mg pure target peptide was finally obtained.
MS (ESI⁺, m/e): 5161.83[M+H]⁺

Example 45 Preparation of Compound 45

Compound 45 was prepared with reference to the method of Example 41.

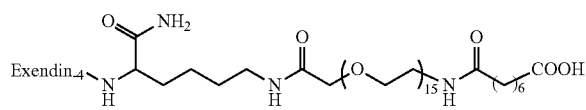

42 mg pure target peptide was finally obtained.
MS (ESI⁺, m/e): 5185.7[M+H]⁺

Example 46 Preparation of Compound 46

Preparation of Exendin-4(1-39)-Orn40(Alloc)-NH$_2$ resin

Taking 5 g Fmoc-Rink MBHA Amide resin, 20% piperidine/DMF was used for the removal of Fmoc, HOBT/DIC was used as the coupling reagent, and the reactive solvent was DMF. The reaction was monitored by employing the ninhydrin detection method, successively connecting the following protected amino acids onto Rink MBHA Amide resin: Fmoc-Orn(Alloc)-OH, Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg (Pbf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Fmoc-His(Trt)-OH, (Boc)$_2$O (using DIEA, dichloromethane). They were washed with DMF washed with methanol, washed with dichloromethane, and then dried to give 7.8 g Exendin-4(1-39)-Orn40(Alloc)-NH$_2$ resin.

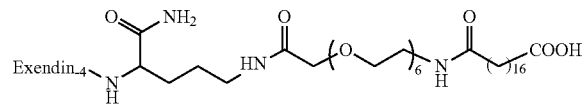

1.5 g Exendin-4(1-39)-Orn40(Alloc)-NH$_2$ resin was swelled in DMF, into which was then added 3 eq solution of Pd(PPh$_3$)$_4$ in CHCl$_3$:AcOH:NMM (18:1:0.5). They were reacted for 2 h, then washed with chloroform (6 times, 20 ml chloroform for each time), washed with 20% solution of HOAc in dichloromethane (6 times, 20 ml 20% solution of HOAc in dichloromethane for each time), washed with dichloromethane (6 times, 20 ml dichloromethane for each time) and washed with DMF (6 times, 20 ml DMF for each time). When it was detected with ninhydrin as positive, 5 ml DMF, 415 mg compound BP103m60, 150 mg HOAT, and 150 ul DIC were added and reacted for 4 h; and when it was detected with ninhydrin as negative, indicting that the side chain BP103m60 has connected onto Exendin-4(1-39)-Orn40-NH$_2$ resin. The pyrolysis of the resin was carried out by employing 82.5% TFA/5% phenol/5% water/2.5% EDT/5% thioanisole, and then they were precipitated with ice-cold methyl tert-butyl ether (MTBE), and washed. Crude products were purified by HPLC to give 41 mg target compound.

MS (ESI⁺, m/e): 4915.61 [M+H]⁺

Example 47 Preparation of Compound 47

Compound 47 was prepared with reference to the method of Example 46.

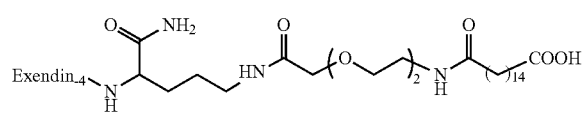

42 mg pure target peptide was finally obtained.
MS (ESI⁺, m/e): 4711.45[M+H]⁺

Example 48 Preparation of Compound 48

Compound 48 was prepared with reference to the method of Example 46.

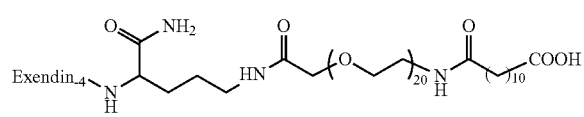

43.4 mg pure target peptide was finally obtained.
MS (ESI⁺, m/e): 5447.91 [M+H]⁺

Example 49 Preparation of Compound 49

Compound 49 was prepared with reference to the method of Example 46.

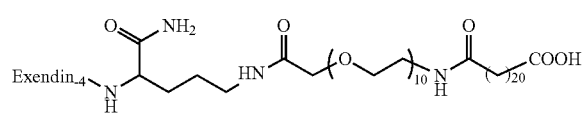

43 mg pure target peptide was finally obtained.
MS (ESI⁺, m/e): 5147.81[M+H]⁺

Example 50 Preparation of Compound 50
Compound 50 was prepared with reference to the method of Example 46.
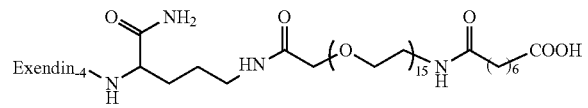
42.8 mg pure target peptide was finally obtained.
MS (ESI$^+$, m/e): 5171.68[M+H]$^+$
Example 51 Preparation of Compound 51
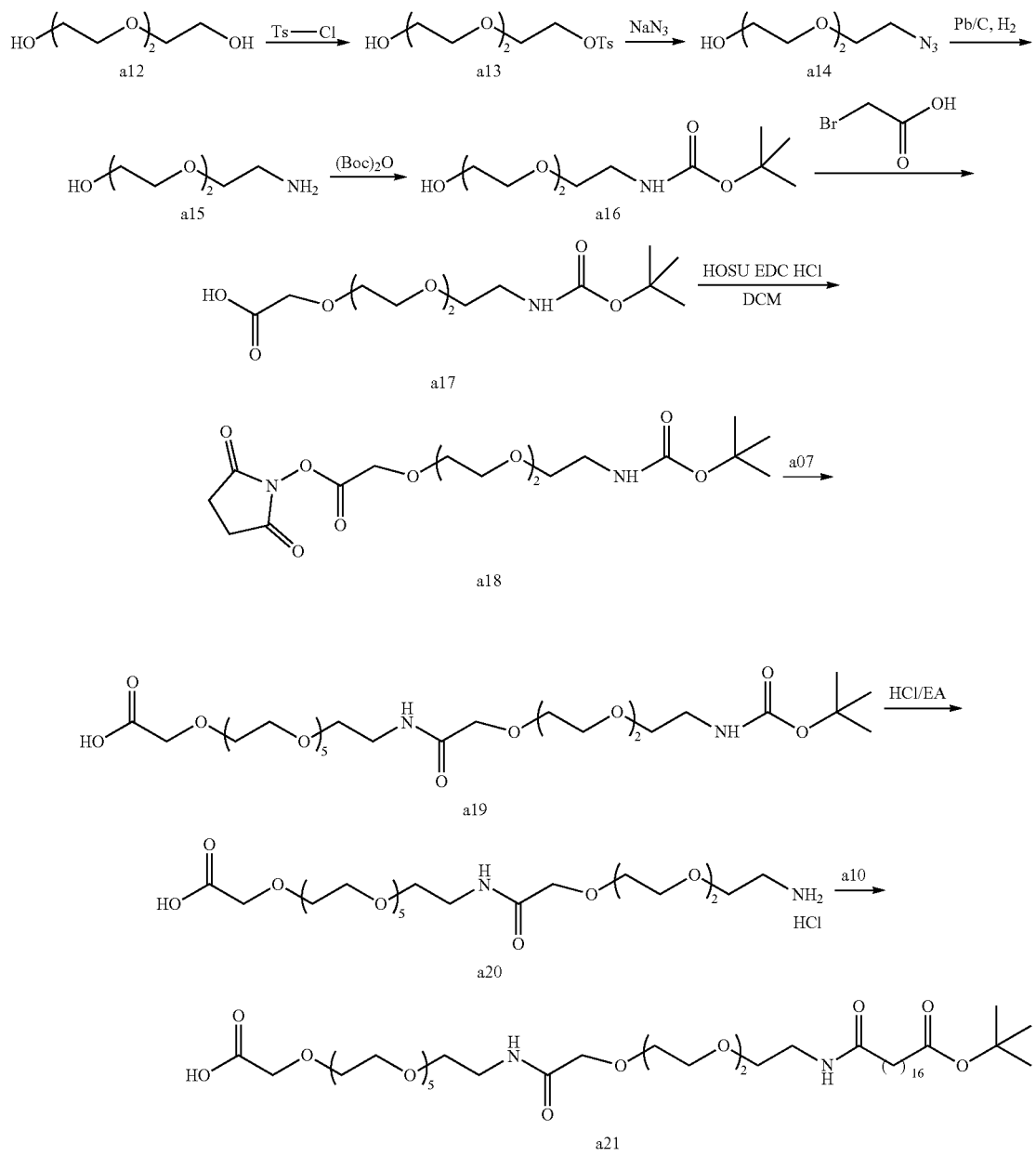

Preparation of Compound a13

Under the protection of nitrogen, to a 1000 ml three-necked flask were added 200 mL pyridine, 120 g a12 (1.0 eq), stirred and cooled down to 0° C. 151.8 g TsCl (1.0 eq) was added in batches, stirred for 1 h, and then slowly warmed up to room temperature, continuing to stir for 3-4 h. After the completion of the reaction, the reaction liquid was poured into the ice-cold solution of dilute hydrochloric acid, with a solid being generated, which was extracted with ethyl acetate. The ethyl acetate layer was washed once with dilute hydrochloric acid, washed with saturated sodium bicarbonate and saturated brine, and dried over anhydrous $Na_2SO_4$. The solvents were evaporated off at reduced pressure to give 119 g crude product, which was chromatographed in a silica gel column to give 55 g pure a13.

Preparation of Compound a14

To a 1000 mL three-necked flask were added 55 g a13 (1.0 eq) and 160 mL DMSO, stirred evenly, then added $NaN_3$ 23.52 g (2.0 eq), heated to 50° C. and reacted for 3 hours, cooled down to room temperature. The reaction liquid was poured into 1.2 L water, extracted with ethyl acetate. The organic phases were combined, dried over anhydrous sodium sulfate, and concentrated to give 29.2 g a14 as a colourless liquid.

Preparation of Compound a15

To a 1 L hydrogenation reactor were added 29 g compound a14, methanol 360 mL, palladium on carbon 5.0 g, stirred, with nitrogen replaced by introducing hydrogen to react for 3-4 h. After the completion of the reaction under the monitor of TLC, the reaction liquid was filtered, and the filtrate was concentrated to give 23.5 g a15 as an oil.

Preparation of Compound a 16

To a 1 L three-necked flask were added 23.5 g compound a15 (1.0 eq), 68.6 g $(Boc)_2O$ (2.0 eq), a mixed solution of methanol:triethylamine (9:1) 500 ml, stirred and warmed to reflux, and reacted for 1 h. After the completion of the reaction under the monitor of TLC, methanol triethylamine was evaporated off, and dissolved in water. Dichloromethane was extracted for 3 times. The organic layers were combined and washed once with water, dried over anhydrous sodium sulfate, evaporated off the solvents, and dried to give 34.8 g a16 as solid.

Preparation of Compound a 17

To a 1000 mL three-necked flask were added 34.8 g compound a16 (1.0 eq), toluene and THF 150 ml for each, bromoacetic acid 58.2 g (3 eq), stirred, heated to 45-50° C., then added sodium hydroxide 33.5 g (6 eq), and reacted overnight. After the completion of the reaction under the monitor of TLC, the reaction liquid was evaporated off, extracted with water and ethyl acetate, and the aqueous phase was adjusted to pH 3. The aqueous phase was extracted with dichloromethane, and the dichloromethane layers were combined, dried over anhydrous sodium sulfate, and then concentrated to give 18 g a17 oily compound.

Preparation of Compound a 18

To a 100 mL three-necked flask were added 286 mg N-hydroxy succinimide (HOSU), 0.50 g a17 and 5 ml dichloromethane, into which was added 477 mg EDC.HCl, and reacted for 2 h at room temperature. After the completion of the reaction under the monitor of TLC, they were diluted with dichloromethane, and then washed with 50 mmol/L aqueous solution of potassium dihydrogen phosphate at pH=6.0 for 2 times, washed with saturated brine, dried over anhydrous sodium sulfate, and concentrated to give 0.72 g compound a18 as an oil.

Preparation of Compound a19

To a 100 mL flask were added 0.62 g compound a07 (1.0 eq), 10 ml water, 0.27 g $NaHCO_3$ (2.0 eq), and stirred. A solution of 0.66 g compound a18 in 10 ml DME (ethylene glycol dimethyl ether) was added dropwise, replenished with 5 ml THF, and stirred overnight. After the completion of the reaction under the monitor of TLC, the organic solvents were evaporated off, adjusted to pH=4 with dilute hydrochloric acid, extracted with dichloromethane, dried over anhydrous sodium sulfate, and concentrated to give 0.71 g compound a19 as an oil.

Preparation of Compound a20

To a 100 mL flask was added 0.71 g compound a19, which was dissolved with 5 ml ethyl acetate and then cooled down to 0° C., with the addition of 5 ml HCl/ethyl acetate (7 mol/L), keeping the temperature at 0° C. After the completion of the reaction under the monitor of TLC, they were concentrated to give 0.71 g a20 as an oil.

Preparation of Compound a2

To a 100 mL flask were added 640 mg compound a20 (1.0 eq), 15 ml water, 190 mg $NaHCO_3$ (2.0 eq), and stirred. A solution of 528 mg compound a10 in 15 ml DME (ethylene glycol dimethyl ether) was added dropwise, replenished with 15 ml THF, and stirred overnight. After the completion of the reaction under the monitor of TLC, the organic solvents were evaporated off, adjusted to pH=6 with acetic acid, extracted with dichloromethane, dried over anhydrous sodium sulfate, and concentrated to give 0.65 g a21 as an oil.

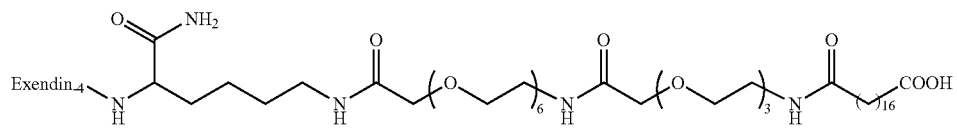

1.5 g Exendin-4(1-39)-Lys40(Alloc)-$NH_2$ resin was swelled in DMF, into which was then added 3 eq solution of $Pd(PPh_3)_4$ in $CHCl_3$:AcOH:NMM (18:1:0.5). They were reacted for 2 h, then washed with chloroform (6 times, 20 ml chloroform for each time), washed with 20% solution of HOAc in dichloromethane (6 times, 20 ml 20% solution of HOAc in dichloromethane for each time), washed with dichloromethane (6 times, 20 ml dichloromethane for each time) and washed with DMF (6 times, 20 ml DMF for each time). When it was detected with ninhydrin as positive, 5 ml DMF, 528 mg compound a21, 150 mg HOAT (1-hydroxy-7-azobenzotriazole), and 150 ul DIC were added and reacted for 4 h; and when it was detected with ninhydrin as negative, indicting that the side chain a21 has connected onto Exendin-4(1-39)-Lys40-$NH_2$ resin. The pyrolysis of the resin was carried out by employing 82.5% TFA/5% phenol/5% water/2.5% EDT/5% thioanisole, and then they were precipitated with ice-cold methyl tert-butyl ether (MTBE), and washed. Crude products were purified by HPLC to give 48 mg target compound.

MS (ESI+, m/e): 5123.50[M+H]+

Example 52 Preparation of Compound 52

Compound 52 was prepared with reference to the method of Example 51.

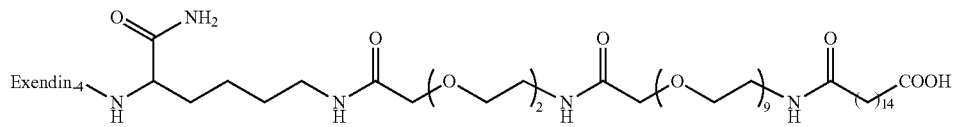

47.5 mg pure target peptide was finally obtained.
MS (ESI$^+$, m/e): 5178.76[M+H]$^+$ Example 53 Preparation of Compound 53

Compound 53 was prepared with reference to the method of Example 51.

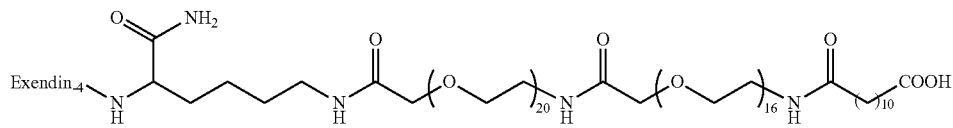

53 mg pure target peptide was finally obtained.
MS (ESI$^+$, m/e): 6223.43[M+H]$^+$ Example 54 Preparation of Compound 54

Compound 54 was prepared with reference to the method of Example 5.

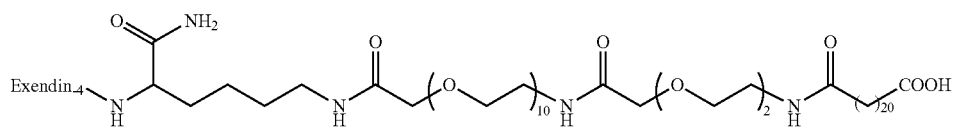

48.3 mg pure target peptide was finally obtained.
MS (ESI$^+$, m/e): 5306.91 [M+H]$^+$ Example 55 Preparation of Compound 55

Compound 55 was prepared with reference to the method of Example 51.

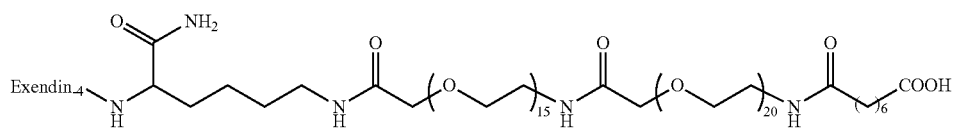

52.8 mg pure target peptide was finally obtained.
MS (ESI$^+$, m/e): 6123.32[M+H]$^+$ Example 56 Preparation of Compound 56

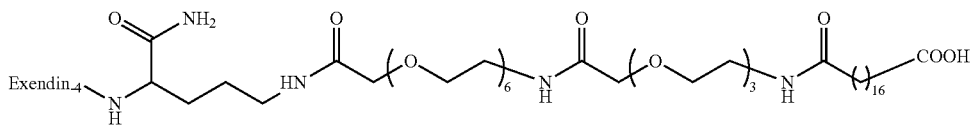

1.5 g Exendin-4(1-39)-Orn40(Alloc)-NH$_2$ resin was swelled in DMF, into which was then added 3 eq solution of Pd (PPh$_3$)$_4$ in CHCl$_3$:AcOH:NMM (18:1:0.5). They were reacted for 2 h, then washed with chloroform (6 times, 20 ml chloroform for each time), 20% solution of HOAc in dichloromethane (6 times, 20 ml 20% solution of HOAc in dichloromethane for each time), washed with dichloromethane (6 times, 20 ml dichloromethane for each time) and washed with DMF (6 times, 20 ml DMF for each time). When it was detected with ninhydrin as positive, 5 ml DMF, 528 mg compound BP103m53, 150 mg HOAT, 150 ul DIC were reacted for 4 h; and when it was detected with ninhydrin as negative, indicting that the side chain BP103m53 has connected onto Exendin-4(1-39)-Orn40-NH$_2$ resin. The pyrolysis of the resin was carried out by employing 82.5% TFA/5% phenol/5% water/2.5% EDT/5% thioanisole, and then they were precipitated with ice-cold methyl tert-butyl ether (MTBE), and washed. Crude products were purified by HPLC to give 47 mg target compound.

MS (ESI$^+$, m/e): 5104.72[M+H]$^+$

Example 57 Preparation of Compound 57

Compound 57 was prepared with reference to the method of Example 56.

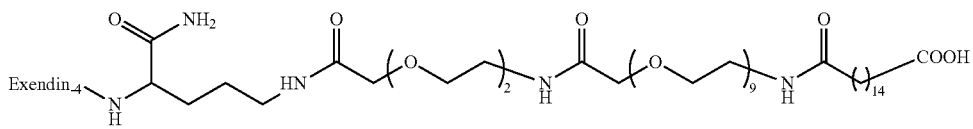

48 mg pure target peptide was finally obtained.
MS (ESI$^+$, m/e): 5164.74[M+H]$^+$ Example 58 Preparation of Compound 58

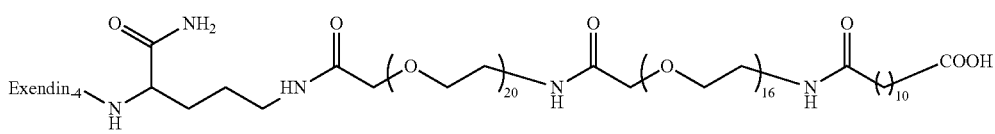

Compound 58 was prepared with reference to the method of Example 56.

51 mg pure target peptide was finally obtained.
MS (ESI⁺, m/e): 6209.41 [M+H]⁺

Example 59 Preparation of Compound 59

Compound 59 was prepared with reference to the method of Example 56.

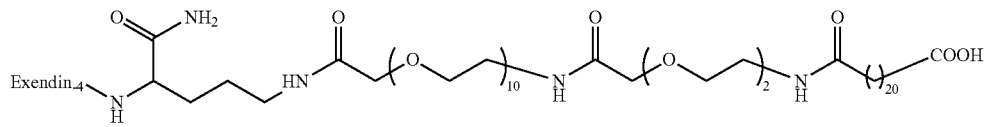

47.6 mg pure target peptide was finally obtained.
MS (ESI⁺, m/e): 5292.89[M+H]⁺

Example 60 Preparation of Compound 60

Compound 60 was prepared with reference to the method of Example 56.

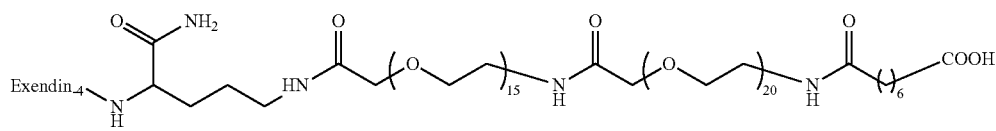

49.7 mg pure target peptide was finally obtained.
MS (ESI⁺, m/e): 6109.3[M+H]⁺

Example 61 Preparation of Compound 61

Preparation of Exendin-4(1-39)-Cys(40)-NH₂

The solid phase peptides of target peptides were synthesized by employing the solid phase synthesis of Fmoc process, using Fmoc-Rink MBHA Amide resin, in which 20% piperidine/DMF was used to remove Fmoc, HOBT/DIC was used as the coupling reagent, and the reactive solvent was DMF. The reaction was monitored by employing the ninhydrin detection method, successively connecting the following protected amino acids onto the Rink MBHA Amide resin: Fmoc-Cys(Trt)-OH, Fmoc-Ser(tBu)-OH, Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH. Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH. Fmoc-Leu-OH, Fmoc-Arg (Pbf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH, Fmoc-His(Trt)-OH, with Fmoc protection finally removed. They were washed with DMF, dichloromethane, and MeOH, and then dried to give resin with fully protection. The pyrolysis of the resin was achieved by employing 82.5% TFA/5% phenol/5% water/2.5% EDT/5% thioanisole, and then they were precipitated with ice-cold methyl tert-butyl ether (MTBE), and washed, and crude products were purified by reverse HPLC to give pure Exendin-4(1-39)-Cys(40)-NH₂.

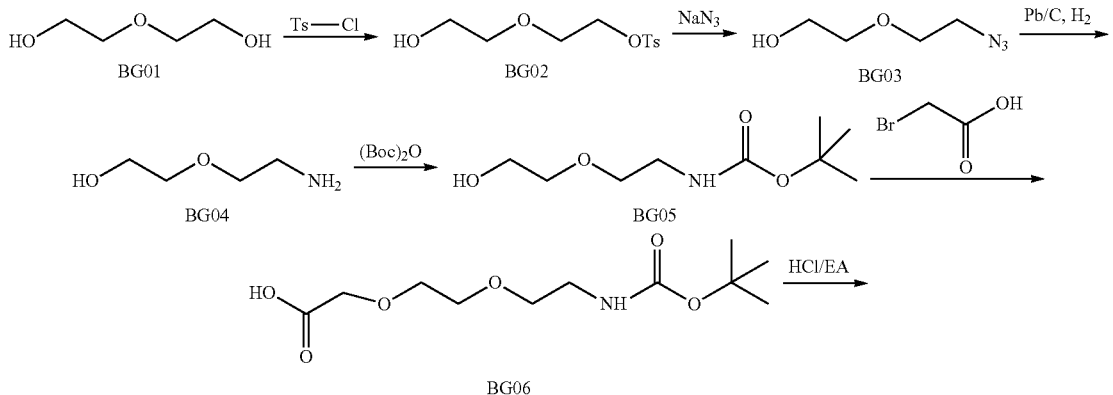

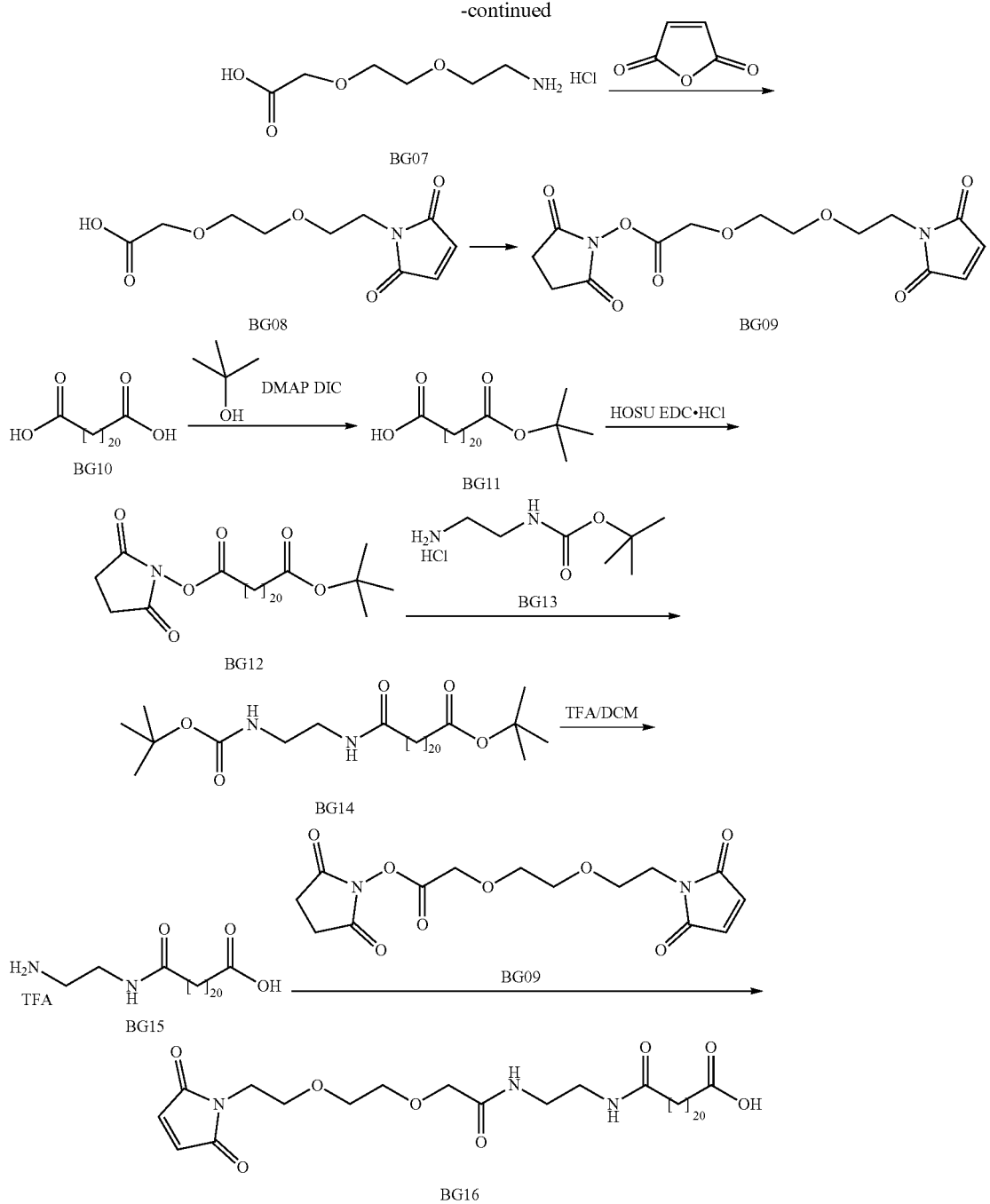

Preparation of BG02

Under the protection of nitrogen, to a 500 ml three-necked flask were added 200 mL pyridine, 18.8 g BG01 (1.0 eq), stirred and cooled down to 0° C. 35.5 g TsCl (1.0 eq) was added in batches, stirred for 1 h, and then slowly warmed up to room temperature, continuing to stir for 3-4 h. After the completion of the reaction, the reaction liquid was poured into the ice-cold solution of dilute hydrochloric acid, with a solid being generated, which was extracted with ethyl acetate. The ethyl acetate layer was washed once with dilute hydrochloric acid, washed with saturated sodium bicarbonate and saturated brine, and dried over anhydrous $Na_2SO_4$. The solvents were evaporated off at reduced pressure, and chromatographed in a silica gel column to give 22.7 g pure BG02.

Preparation of BG03

To a 500 mL three-necked flask were added 22.7 g BG02 (1.0 eq) and 190 mL DMSO, stirred evenly, then added $NaN_3$ 11.5 g (2.0 eq), heated to 50° C. and reacted for 3 hours, cooled down to room temperature. The reaction liquid was poured into water, extracted with ethyl acetate for many times. The organic phases were combined, dried over anhydrous sodium sulfate, and concentrated to give 17.1 g BG03 as a colourless liquid.

Preparation of BG04

To a 1 L hydrogenation reactor were added BG03 30 g, methanol 500 mL, palladium on carbon 8.0 g, stirred, with nitrogen replaced by introducing hydrogen to react for 3-4 h. After the completion of the reaction under the monitor of TLC, the reaction liquid was filtered, and the filtrate was concentrated to give 19.4 g BG04 as an oil.

Preparation of BG05

To a 500 mL three-necked flask were added compound BG04 3.7 g (1.0 eq), (Boc)$_2$O 15.5 g (2.0 eq), a mixed solution of methanol:triethylamine (9:1) 200 ml, stirred and warmed to reflux, and reacted for 1 h. After the completion of the reaction under the monitor of TLC, methanol triethylamine was evaporated off, and dissolved in water. Dichloromethane was extracted for 3 times. The organic layers were combined and washed once with water, dried over anhydrous sodium sulfate, and concentrated to give 4.8 g BG05 as an oil.

Preparation of BG06

To a 250 mL three-necked flask were added BG05 compound 3.7 g (1.0 eq), toluene and THF 40 ml for each, bromoacetic acid 7.6 g (3.0 eq), stirred, heated to 45-50° C., then added sodium hydroxide 4.4 g, and reacted overnight. After the completion of the reaction under the monitor of TLC, the reaction liquid was evaporated off, the impurities were extracted with water and ethyl acetate, and the aqueous phase was adjusted to pH=3. The aqueous phase was extracted with dichloromethane, and the dichloromethane layers were combined, dried over anhydrous sodium sulfate, and then concentrated to give 2.5 g BG06 oily compound.

Preparation of BG07

To a 100 mL single-neck flask were added 2.4 g compound BG06 and 20 ml ethyl acetate, after being dissolved, they were cooled down to 0° C., into which was added 20 ml HCl/ethyl acetate (7 mol/L). After the completion of the reaction under the monitor of TLC, they were concentrated to give 2.3 g BG07 as an oil.

Preparation of BG08

To a 200 mL three-necked flask were added 3.5 g compound BG07 (1.0 eq), 1.7 g maleic anhydride (1.0 eq), 70 ml acetic acid, and heated to reflux overnight. After the completion of the reaction under the monitor of TLC, the acetic acid was evaporated off, into which was added ethyl acetate to dissolve, and then washed with water for 3 times, washed with saturated sodium chloride for 3 times, dried over anhydrous sodium sulfate, and chromatographed in a column to give 1.8 g BG08 as an off-white solid.

Preparation of BG09

To a 100 mL three-necked flask were added 1.30 g (1.53 eq) N-hydroxy succinimide (HOSU), 3.1 g compound, BG08 1.8 g and 15 ml dichloromethane, into which was added 2.16 g EDC.HCl (1.53 eq) and reacted for 2 h at room temperature. After the completion of the reaction under the monitor of TLC, they were diluted with dichloromethane, and then washed with 50 mmol/L aqueous solution of potassium dihydrogen phosphate at pH=6.0 for 2 times, washed with saturated brine, dried over anhydrous sodium sulfate, and concentrated to give 2.2 g off-white compound BG09.

Preparation of BG11

To a 50 mL three-necked flask were added 2.17 g compound BG10 (1.0 eq), 10 ml dichloromethane, 10 ml tert-butanol, 0.40 g DIC (1.0 eq), and 0.39 g DMAP (1.0 eq), and stirred at room temperature overnight. After the completion of the reaction under the monitor of TLC, they were diluted with ether, and then washed with water for 3 times, washed with saturated brine, dried over anhydrous sodium sulfate, and chromatographed in a column to give 0.6 g foamy powder BG11.

Preparation of BG12

To a 100 mL three-necked flask were added 0.95 g N-hydroxy succinimide (HOSU), 3.1 g compound BG11 and 15 ml dichloromethane, into which was added 1.58 g EDC-HCl, and reacted for 2 h at room temperature. After the completion of the reaction under the monitor of TLC, they were diluted with dichloromethane, and then washed with 50 mmol/L aqueous solution of potassium dihydrogen phosphate at pH=6.0 for 2 times, washed with saturated brine, dried over anhydrous sodium sulfate, and concentrated to give 3.3 g compound BG12 as a white solid.

Preparation of BG14

To a 200 mL flask were added 2.8 g compound BG13 (1.05 eq), 50 ml water, 1.8 g NaHCO$_3$ (2.0 eq), and stirred. A solution of 6.4 g compound BG12 (1.0 eq) in 50 ml DME (ethylene glycol dimethyl ether) was added dropwise, replenished with 50 ml THF, and stirred overnight. After the completion of the reaction under the monitor of TLC, the organic solvents were evaporated off, adjusted to pH=4 with acetic acid, extracted with ethyl acetate, dried over anhydrous sodium sulfate, and concentrated to give 6.9 g compound BG14 as an off-white solid.

Preparation of BG15

To a 100 mL flask were added 6.9 g compound BG14, 30 ml dichloromethane, 30 ml TFA, and stirred at 20° C. After the completion of the reaction under the monitor of TLC, the organic solvents were evaporated off, slurried with petroleum ether, suction filtrated, and dried to give 5.35 g BG15 as an off-white solid.

Preparation of BG16

To a 100 mL flask were added 1.27 g compound BG15 (1.0 eq), 10 ml water, 0.36 g NaHCO$_3$ (2.0 eq), and stirred. A solution of 0.72 g compound BG09 (1.0 eq) in 10 ml DME (ethylene glycol dimethyl ether) was added dropwise, replenished with 10 ml THF, and stirred overnight. After the completion of the reaction under the monitor of TLC, the organic solvents were evaporated off, adjusted to pH=6 with acetic acid, and extracted with ethyl acetate. The organic phases were washed with water and saturated brine, and then dried over anhydrous sodium sulfate, concentrated, and chromatographed in a column to give 0.9 g compound BG16 as an off-white solid.

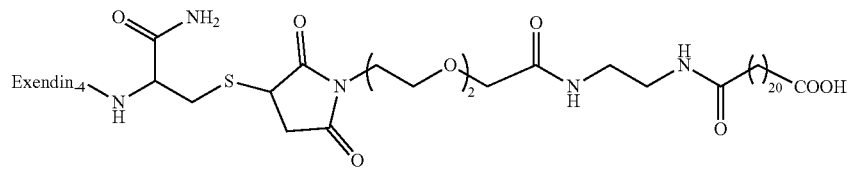

50.0 mg Exendin-4(1-39)-Cys(40)-NH$_2$ was dissolved in 10 ml sodium phosphate buffer (pH 6.5) at 20 mM, into which was added 16 mg BG16 and stirred for 1 hour at the condition of 20° C. After the completion of the reaction under the monitor of HPLC, the reaction was stopped with excess cysteine solution (0.5 ml 0.5M cysteine solution), prepared with HPLC and then lyophilized to give 30 mg coupling compound.

MS (ESI$^+$, m/e): 4926.49[M+H]$^+$.

Example 62 Preparation of Compound 62

Compound 62 was prepared with reference to the method of Example 61.

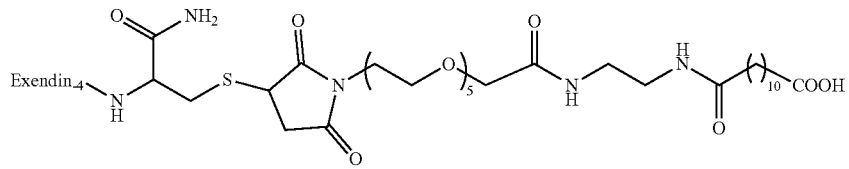

Crude products were purified by HPLC to give 31 mg target compound.
MS (ESI$^+$, m/e): 4918.41 [M+H]$^+$.

Example 63 Preparation of Compound 63

Compound 63 was prepared with reference to the method of Example 61.

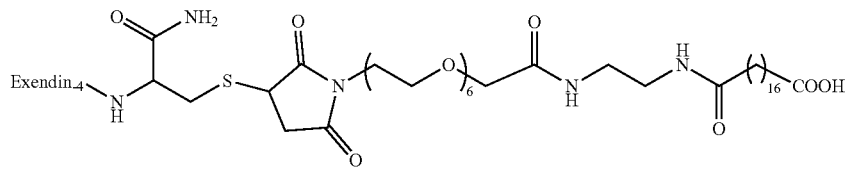

Crude products were purified by HPLC to give 31 mg target compound.
MS (ESI$^+$, m/e): 5046.53[M+H]$^+$.

Example 64 Preparation of Compound 64

Compound 64 was prepared with reference to the method of Example 61.

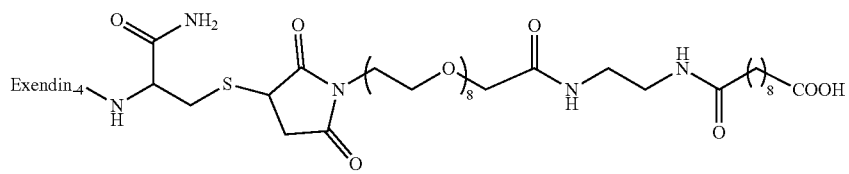

Crude products were purified by HPLC to give 29 mg target compound.
MS (ESI⁺, m/e): 5022.46[M+H]⁺.

Example 65 Preparation of Compound 65

Compound 65 was prepared with reference to the method of Example 61.

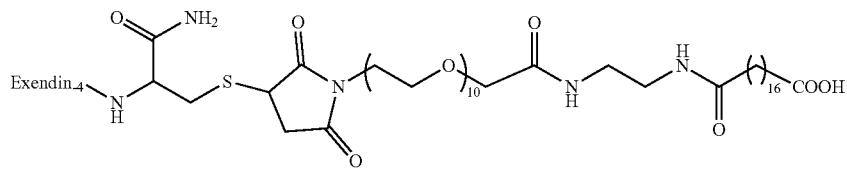

Crude products were purified by HPLC to give 34 mg target compound.
MS (ESI⁺, m/e): 5222.63[M+H]⁺.

Example 66 Preparation of Compound 66

Compound 66 was prepared with reference to the method of Example 61.

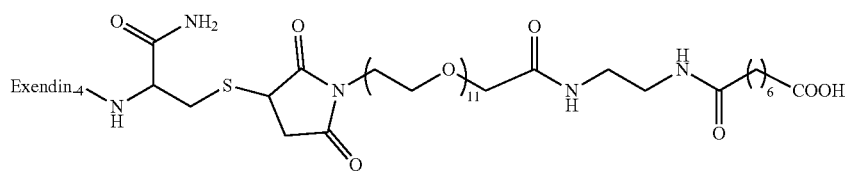

Crude products were purified by HPLC to give 32 mg target compound.
MS (ESI⁺, m/e): 5126.5[M+H]⁺.

Example 67 Preparation of Compound 67

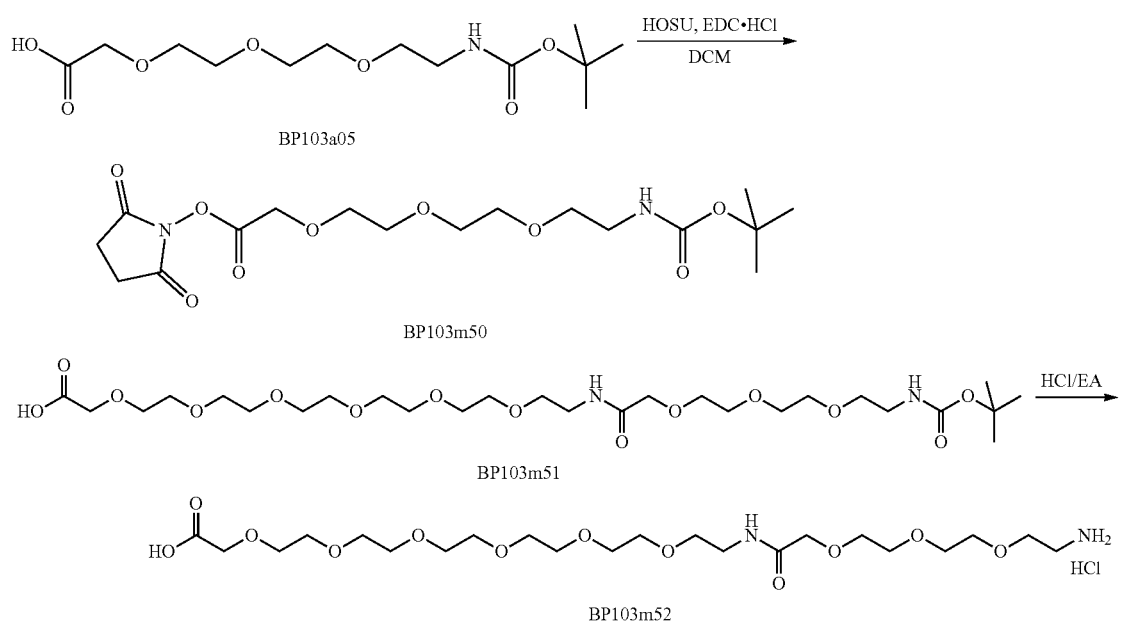

Preparation of Compound BP103m50

To a 100 mL three-necked flask were added 286 mg N-hydroxy succinimide (HOSU), 0.50 g BP103a05 and 5 ml dichloromethane, into which was added 477 mg EDC.HCl and reacted for 2 h at room temperature. After the completion of the reaction under the monitor of TLC, they were diluted with dichloromethane, and then washed with 50 mmol/L aqueous solution of potassium dihydrogen phosphate at Ph=6.0 for 2 times, washed with saturated brine, dried over anhydrous sodium sulfate, and concentrated to give 0.72 g compound BP103m50 as an oil.

Preparation of compound BP103m51

To a 100 mL flask were added 0.62 g compound BP103g06 (1.0 eq), 10 ml water, 0.27 g NaHCO$_3$ (2.0 eq), and stirred. A solution of 0.66 g compound BP103m50 in 10 ml DME (ethylene glycol dimethyl ether) was added dropwise, replenished with 5 ml THF, and stirred overnight. After the completion of the reaction under the monitor of TLC, the organic solvents were evaporated off, adjusted to pH=4 with dilute hydrochloric acid, extracted with dichloromethane, dried over anhydrous sodium sulfate, and concentrated to give 0.71 g compound BP103m51 as an oil.

Preparation of Compound BP103m52

To a 100 mL flask were added 0.71 g compound BP103m51 and 5 ml ethyl acetate, after being dissolved, they were cooled down to 0° C., into which was added 5 ml HCl/ethyl acetate (7 mol/L), keeping the temperature at 0° C. After the completion of the reaction under the monitor of TLC, they were concentrated to give 0.71 g BP103m52 as an oil.

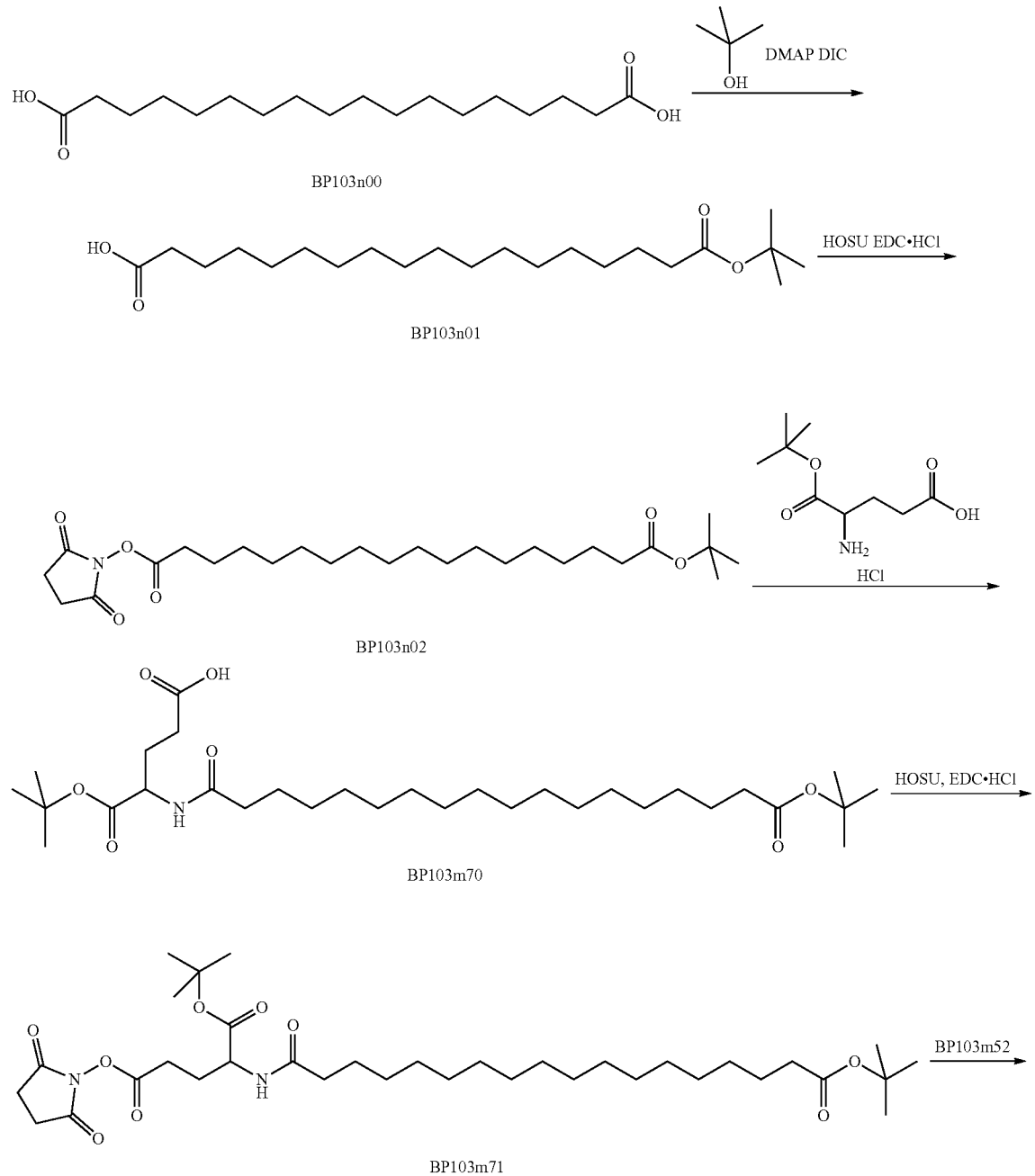

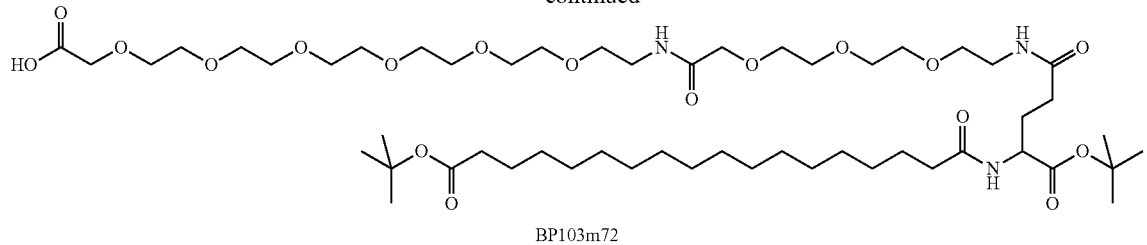

BP103m72

Preparation of Compound BP103n01

To a 50 mL three-necked flask were added 1.0 g compound BP103n00 (1.0 eq), 10 ml dichloromethane, 10 ml tert-butanol, 0.40 g DIC (1.0 eq), and 0.39 g DMAP (1.0 eq), and stirred overnight at room temperature. After the completion of the reaction under the monitor of TLC, they were diluted with ether, and washed with water for 3 times, washed with saturated brine, dried over anhydrous sodium sulfate, and chromatographed in a column to give 0.4 g BP103n01 as a foamy powder.

Preparation of compound BP103n02

To a 100 mL three-necked flask were added 0.95 g N-hydroxy succinimide (HOSU), 2.0 g compound BP103n01 and 15 ml dichloromethane, into which was added 1.58 g EDC.HCl and reacted for 2 h at room temperature. After the completion of the reaction under the monitor of TLC, they were diluted with dichloromethane, and then washed with 50 mmol/L aqueous solution of potassium dihydrogen phosphate at pH=6.0 for 2 times, washed with saturated brine, dried over anhydrous sodium sulfate, and concentrated to give 2.6 g compound BP103n02 as a white solid.

Preparation of Compound BP103m70

To a 100 mL flask were added 0.50 g compound H-Glu-OtBu.HCl (1.0 eq), 10 ml water, 350 mg NaHCO$_3$ (2.0 eq), and stirred. A solution of 0.96 g compound BP103n02 (1.0 eq) in 10 ml DME (ethylene glycol dimethyl ether) was added dropwise, replenished with 10 ml THF, and stirred overnight. After the completion of the reaction under the monitor of TLC, the organic solvents were evaporated off, adjusted to pH=6 with acetic acid, extracted with dichloromethane, dried over anhydrous sodium sulfate, and concentrated to give 1.09 g compound BP103m70 as an oil.

Preparation of Compound BP103m71

To a 100 mL three-necked flask were added 1.0 g compound BP103m70, 317 mg N-hydroxy succinimide (HOSU) (1.53 eq), and 10 ml dichloromethane, into which was added 528 mg EDC.HCl (1.53 eq) and reacted for 2 h at room temperature. After the completion of the reaction under the monitor of TLC, they were diluted with dichloromethane, and then washed with 50 mmol/L aqueous solution of potassium dihydrogen phosphate at pH=6.0 for 2 times, washed with saturated brine, dried over anhydrous sodium sulfate, and concentrated to give 1.07 g compound BP103m71 as a white solid.

Preparation of Compound BP103m72

To a 100 mL flask were added 0.87 g compound BP03m52 (1.0 eq), 10 ml water, 300 mg NaHCO$_3$ (2.0 eq), and stirred. A solution of 1.00 g compound BP103m71 (1.0 eq) in 10 ml DME (ethylene glycol dimethyl ether) was added dropwise, replenished with 10 ml THF, and stirred overnight. After the completion of the reaction under the monitor of TLC, the organic solvents were evaporated off, adjusted to pH=6 with acetic acid, extracted with dichloromethane, dried over anhydrous sodium sulfate, and concentrated to give 1.22 g compound BP03m72 as an oil.

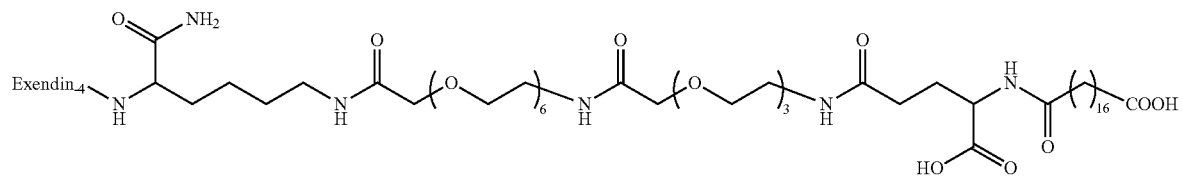

Synthesis of Target Peptide 1.5 g Exendin-4(1-39)-Lys40(Alloc)-NH$_2$ resin was swelled in DMF, into which was then added 3 eq solution of Pd (PPh$_3$)$_4$ in CHCl$_3$:AcOH:NMM (18:1:0.5). They were reacted for 2 h, then washed with chloroform (6 times, 20 ml chloroform for each time), washed with 20% solution of HOAc in DCM (dichloromethane) (6 times, 20 ml 20% solution of HOAc in DCM for each time), washed with DCM (6 times, 20 ml DCM for each time) and washed with DMF (6 times, 20 ml DMF for each time). When it was detected with ninhydrin as positive, 5 ml DMF, 640 mg compound BP103m72, 150 mg HOAT, and 150 ul DIC were added and reacted for 4 h; and when it was detected with ninhydrin as negative, indicting that the side chain BP103m72 has connected onto Exendin-4(1-39)-Lys40-NH$_2$ resin. The pyrolysis of the resin was carried out by employing 82.5% TFA/5% phenol/5% water/2.5% EDT/5% thioanisole, and then they were precipitated with ice-cold methyl tert-butyl ether (MTBE), and washed. Crude products were purified by HPLC to give 48 mg target compound.

MS (ESI$^+$, m/e): 5252.54[M+H]$^+$.

wherein the modified exendin-4 is:

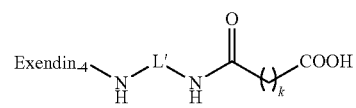

k is any integer between 6-20,
wherein L is selected from the group consisting of:

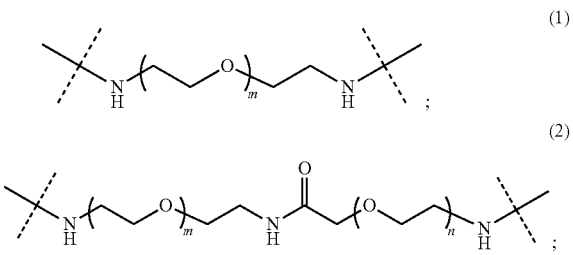

---

---

The invention claimed is:

1. A modified exendin-4 or pharmaceutically acceptable salts thereof, as shown in formula (I):

(Ex-4)-L-Y          (I)

wherein, Ex-4 is Exendin-4; L is

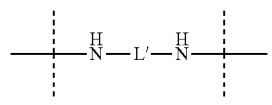

for connecting Ex-4 with Y; L' is a hydrophilic linking arm; Y is an aliphatic chain with a terminal carboxyl group, -continued

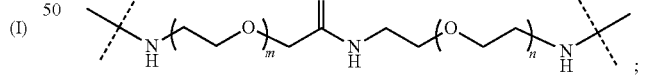

-continued
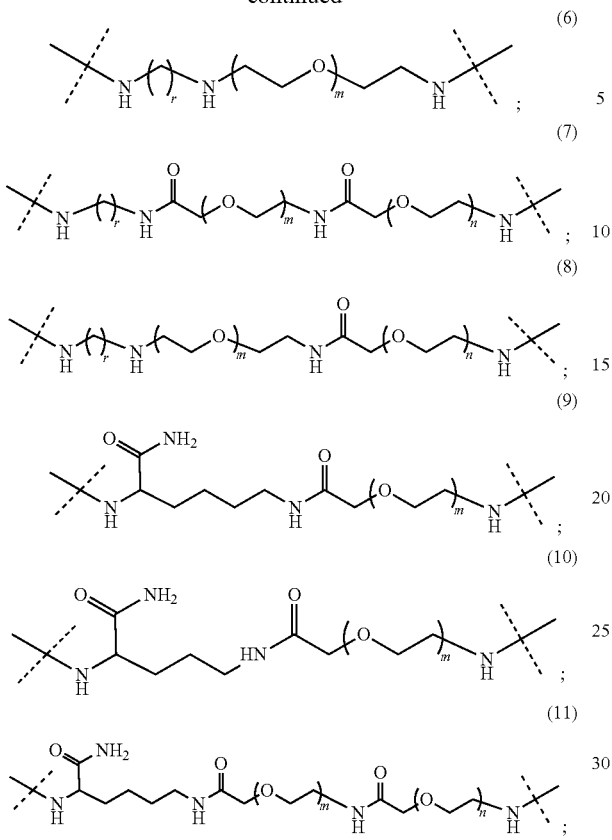
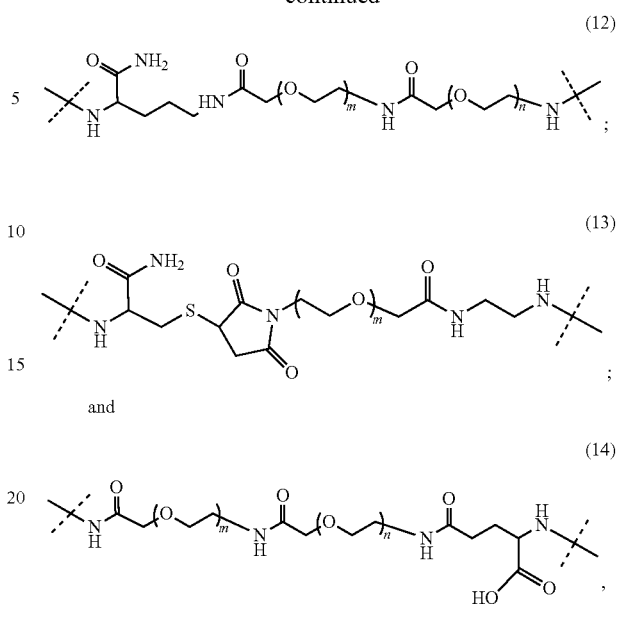
wherein, m is any integer between 2-20; n is any integer between 2-20; r is any integer between 1-6.
2. A pharmaceutical composition comprising the modified exendin-4 or pharmaceutically acceptable salts thereof according to claim 1 and optionally pharmaceutically acceptable carriers.
* * * * *